(12) United States Patent
Shusterman

(10) Patent No.: US 7,801,591 B1
(45) Date of Patent: *Sep. 21, 2010

(54) DIGITAL HEALTHCARE INFORMATION MANAGEMENT

(76) Inventor: Vladimir Shusterman, 245 Mellwood Ave., Apt 501, Pittsburgh, PA (US) 15213

( * ) Notice: Subject to any disclaimer, the term of this patent is extended or adjusted under 35 U.S.C. 154(b) by 844 days.

This patent is subject to a terminal disclaimer.

(21) Appl. No.: 11/641,268

(22) Filed: Dec. 20, 2006

Related U.S. Application Data

(63) Continuation-in-part of application No. 10/816,638, filed on Apr. 2, 2004, now Pat. No. 7,343,197, which is a continuation-in-part of application No. 10/124,651, filed on Apr. 17, 2002, now Pat. No. 6,925,324, which is a continuation-in-part of application No. 09/583,668, filed on May 30, 2000, now Pat. No. 6,389,308.

(51) Int. Cl.
*A61B 1/00* (2006.01)
(52) U.S. Cl. ...................... 600/509; 600/300
(58) Field of Classification Search ............... 600/300, 600/508–523
See application file for complete search history.

(56) References Cited

U.S. PATENT DOCUMENTS

| | | | |
|---|---|---|---|
| 4,193,393 A | 3/1980 | Schlager | |
| 4,679,144 A | 7/1987 | Cox et al. | |
| 5,033,475 A | 7/1991 | Ueda et al. | |
| 5,463,547 A | 10/1995 | Asada et al. | |
| 5,501,229 A | 3/1996 | Selker et al. | |
| 5,544,044 A | 8/1996 | Leatherman | |

(Continued)

OTHER PUBLICATIONS

V. Shusterman and O. Trofimov, Building and Application of Expert Systems for Differential Diagnostics of Cardiovascular Diseases, SAMS, 1994, vol. 14, pp. 15-24.

(Continued)

*Primary Examiner*—Scott M Getzow
(74) *Attorney, Agent, or Firm*—Eckert Seamans Cherin & Mellott, LLC; David V. Radack, Esq.; David W. Brownlee, Esq.

(57) ABSTRACT

System for diagnosis, medical decision support, and healthcare information management that performs analysis of serial health data, adapts to the individual data, and represents dynamics of the most significant parameters (indicators), using at least two scales. The system uses the first-scale (low-resolution) analysis of a snapshot measurement of at least one indicator (primary element) such as heart rate or blood pressure and uses a second-scale (higher-resolution) analysis to determine serial changes in each of the said primary elements. The system optimizes information flow, usage of medical knowledge, and improves accuracy of analysis of serial changes, and adaptability to each individual's data. The information can be distributed in parallel to separate databases at different locations.

50 Claims, 14 Drawing Sheets

U.S. PATENT DOCUMENTS

| | | |
|---|---|---|
| 5,594,638 A | 1/1997 | Iliff |
| 5,724,983 A | 3/1998 | Selker et al. |
| 5,941,820 A | 8/1999 | Zimmerman |
| 5,956,013 A | 9/1999 | Raj et al. |
| 5,967,995 A | 10/1999 | Shusterman et al. |
| 6,038,439 A | 3/2000 | Rune |
| 6,108,635 A | 8/2000 | Herren et al. |
| 6,126,596 A | 10/2000 | Freedman |
| 6,188,988 B1 | 2/2001 | Barry et al. |

OTHER PUBLICATIONS

William G. Baxt, MD et al., A Neural Network Aid for the Early Diagnosis of Cardiac Ischemia in Patients Presenting to the Emergency Department With Chest Pain, Annals of Emergency Medicine, Dec. 2002, pp. 575-583.

Hongmei Yan et al., The internet-based knowledge acquisition and management method to construct large-scale distrbuted medical expert systems, Computer Methods and Programs in Biomedicine (2004) 74, pp. 1-10.

Scale I

| Heart Rate<br>A<br>43 | Beat<br>N<br>sinus | Axis<br>N<br>60 | PR-interval<br>N<br>0.15 | P-amplitude<br>N<br>0.03 |
|---|---|---|---|---|
| QRS-duration<br>N<br>0.1 | Q-amplitude<br>N<br>0.2 | R-amplitude<br>N<br>0.8 | S-amplitude<br>N<br>0.2 | T-amplitude<br>N<br>0.3 |
| ST-segment<br>N<br>0.0 | QT-interval<br>N<br>0.4 | | | |

FIG. 3.

Scale I

| | | | | |
|---|---|---|---|---|
| Heart Rate<br>C<br>63 | Beat<br>U<br>sinus | Axis<br>U<br>60 | PR-interval<br>U<br>0.15 | P-amplitude<br>U<br>0.03 |
| QRS-duration<br>U<br>0.1 | Q-amplitude<br>U<br>0.2 | R-amplitude<br>U<br>0.8 | S-amplitude<br>U<br>0.2 | T-amplitude<br>U<br>0.3 |
| ST-segment<br>U<br>0.0 | QT-interval<br>U<br>0.4 | | | |

FIG. 4.

| Scale I | | | | |
|---|---|---|---|---|
| Heart Rate<br>N<br>67 | Beat<br>N<br>sinus | Axis<br>N<br>50 | PR-interval<br>N<br>0.12 | P-amplitude<br>N<br>0.014 |
| QRS-duration<br>N<br>0.11 | Q-amplitude<br>A<br>0.38 | R-amplitude<br>N<br>1.0 | S-amplitude<br>N<br>0.2 | T-amplitude<br>N<br>0.1 |
| ST-segment<br>N<br>0.0 | QT-interval<br>A<br>0.58 | | | |

FIG. 8.

Scale I

| Heart Rate<br>U<br>67 | Beat<br>U<br>sinus | Axis<br>U<br>50 | PR-interval<br>U<br>0.12 | P-amplitude<br>U<br>0.014 |
|---|---|---|---|---|
| QRS-duration<br>U<br>0.11 | Q-amplitude<br>U<br>0.38 | R-amplitude<br>U<br>1.0 | S-amplitude<br>U<br>0.2 | T-amplitude<br>C<br>-0.35 |
| ST-segment<br>C<br>-0.02 | QT-interval<br>U<br>0.58 | | | |

FIG. 10.

Duration of QT-interval [ms]

DIGITAL HEALTHCARE INFORMATION MANAGEMENT

CROSS-REFERENCE TO RELATED APPLICATION

This is a continuation-in-part of application Ser. No. 10/816,638, filed Apr. 2, 2004, which is a continuation-in-part of application Ser. No. 10/124,651, filed Apr. 17, 2002, now U.S. Pat. No. 6,925,324, which was a continuation-in-part of application Ser. No. 09/583,668, filed May 30, 2000, now U.S. Pat. No. 6,389,308.

FIELD OF THE INVENTION

This invention relates to the field of medical information management, diagnosis, and decision support and more specifically to a method and system for analyzing medical or health data and its serial changes, combining general medical knowledge with individual subject's data and its serial changes, and optimizing the information flow, structuring and representing the results.

BACKGROUND OF THE INVENTION

Medical decision process has been traditionally considered unstructured and ill-posed. Indeed, the ill-posed nature of medical diagnosis and decision making has given rise to the perception that medical diagnosis is a form of art, which cannot be quantified or structured. The main difficulties of medical decision making are related to the following key issues.

First, the nature of medical information processing is inherently probabilistic with a large number of possible diseases, disease stages, side-effects, complications, etc. These possibilities can be alternative, additive, complementary, correlated, partially correlated, or uncorrelated. For example, a pain in the chest area can be caused by heart disease, stomach ulcer, back problems, hypochondriac, neurological conditions, or various combinations of these disorders. In addition, a person might have a combination of different diseases that are not related to the symptoms being investigated but, nevertheless, might change the patient's symptoms and obscure diagnosis. For example, a combination of heart angina and back pain might be difficult to differentiate, because both diseases might have similar symptoms.

Second, there is enormous individual variability in the expression of diseases, which creates completely different profiles of the same illness in different subjects. For example, myocardial infarction (heart attack) can be manifested by pain in the upper left area of the chest, the central region of the chest, left arm, back, or shortness of breath.

Third, incompleteness of information represents a significant problem in medical decision making. In particular, information about different diagnostic tests performed at different times can be distributed among different databases located in different medical institutions. For example, a surgical procedure performed two years ago can be located in that hospital's database, whereas subsequent tests were performed in a different hospital and are located in that hospital's database. Some of the local databases distributed among different medical institutions may be temporarily or permanently unavailable. Thus, a mechanism is needed to estimate the total information completeness, and this information completeness needs to be tracked dynamically, as new information becomes available over time.

Due to these reasons, the "art" of medical diagnosis has traditionally been considered as an ability to weight all probable causes of illness in the shortest possible time in order to start an appropriate treatment as early as possible.

Recent developments of computer and network technologies have created a technological background for incorporation of the ill-posed medical decision making rules and facts into computer and network algorithms. A number of studies have examined this problem, using statistical analysis, pattern recognition, neural networks, and expert systems. For example, application of methods of artificial intelligence for medical diagnosis have been described by Shusterman et al. in Building an application of Expert Systems For Differential Diagnostics of Cardiovascular Diseases, SAMS, 1994, Vol. 14, pp. 15-24, Yan et al. in The Internet-based Knowledge Acquisition and Management Method to Construct Large-scale Distributed Medical Expert Systems, Comput Methods Programs Biomed. 2004 April; 74(1): 1-10, and Baxt et al. in A Neural Network Aid for the Early Diagnosis of Cardiac Ischemia in Patients Presenting to the Emergency Department with Chest Pain, Annals of Emergency Medicine, December 2002 40:06, among other publications.

Various techniques for computerized identification and analysis of health data are also described in several United States patents. For example, Barnhill et al. in the U.S. Pat. No. 6,882,990, (2005) discloses methods of identifying biological patterns using multiple data sets. Using learning process on the training data, optimal solutions are determined for the identification of patterns that are important for medical diagnosis, prognosis and treatment. Bardy in the U.S. Pat. No. 6,887,201 (2005) describes system and method for determining a reference baseline of regularly retrieved patient information for automated remote patient care. The method uses a database of patient records to determine a set of reference measures. Asada et al. in U.S. Pat. No. 5,463,548 (1995) disclose a method and system for differential diagnosis based on clinical and radiological information using artificial neural networks. The method uses radiographic data and clinical information to differentiate mammographic images and lung diseases. Leatherman in the U.S. Pat. No. 5,544,044 (1996) discloses a method for evaluation of health care quality using analysis of health care claims records to assess the quality of care based on conformance to nationally recognized medical practice guidelines or quality indicators and to provide a means to supplement claims with data from patient medical records. Iliff in the U.S. Pat. Nos. 5,594,638 (1997), 5,868,669 (1999), 6,113,540 (2000), 6,206,829 (2001), 6,482,156 (2002), and 6,849,045 (2005) disclose systems and methods for providing computerized, knowledge-based medical diagnostic and treatment advice. "Meta" functions for pattern matching and time-density analysis are included to determine the similarity and the number of medical complaints per unit of time. A re-enter feature monitors the user's changing condition over time. A symptom severity analysis helps to respond to the changing conditions. System sensitivity factors may be changed to adjust the system advice as necessary. Zimmerman in the U.S. Pat. No. 5,941,820 (1999) discloses a method for measuring patient data, determining statistics from the data, variation within the data, homeostasis, modifying control chart limits based on the measure of homeostasis and displaying the statistic on the modified control chart. The control charts are modified as data varies over time. By determining the amount of consistency or similarity using autocorrelation or serial correlation, significant changes are identified. Herren et al. in the U.S. Pat. No. 6,108,635 (2000) discloses a system for drug discovery, design of clinical trials, performing pharmacoeconomic analysis, and illustrating disease progression over time. Freedman in the U.S. Pat. No. 6,126,596 (2000) discloses a system for collecting data and using these data for diagnosis and lookup of appropriate treatments. Barry et al. in the U.S. Pat. No. 6,188,988 (2001) disclose systems, methods and computer program products for guiding the selection of treatment, which comprise (a) providing patient information to a computing device (a knowledge base and expert rules for selecting treatment and advisory information; (b) generating a listing of treatments; and (c) generating advisory information. Papageorge in the U.S. Pat. No. 6,584,445 (2003) discloses a computerized health evaluation system for joint patient-physician decision making. The system includes a patient input module, a physician input module, and a database of medical information about diseases. The computer system uses an algorithm for weighing the patient data and the physician data and generating a report with various treatment options. Sadeghi et al. in the U.S. Pat. No. 6,687,685 (2004) discloses a system and method for automated medical decision-making, such as online, questionnaire-based medical triage. Information is modeled in a Bayesian Network, and the conditional probability may be determined in a real-time.

SUMMARY OF THE INVENTION

This invention provides a method and system that can be used for at least one of information management, decision support, and diagnosis. The method and system distribute (structure) the information into at least two levels of detail (scales or resolutions). A low-resolution scale represents a snapshot measurement of at least one indicator (vital sign or primary element) such as heart rate or blood pressure. A higher resolution scale is designed to determine serial changes in each of the said primary elements. Low, intermediate and high-resolution scales can exchange information between each other for improving the analyses; the scales can be distributed vertically among the units connected by a network and defined according to the corresponding software and hardware resources. Uncertainty or probability of a diagnosis is tracked dynamically (the probabilities are updated periodically or quasi-periodically over time taking into account information available at each time point; new information is included in the analysis as it becomes available) based on the information availability or completeness relative to the total complete information at each level and at multiple levels. This structuring provides several advantages. First, it improves and optimizes the flow of information along the network. This feature is significant, since the volume of information provided by a multitude of diagnostic tests is high (such as electrocardiographic monitoring, magnetic resonance imaging (MRI), computer tomography (CT), CAT-scans, echocardiography, biochemical, and other tests) and increases with time. The structuring permits control this high volume of information, so the most important information (vital signs) is analyzed on-line and on-site (Low-resolution), whereas the rest of the information, which includes subtle changes in patient's state, are detected and quantified using comparative analysis of serial data (Higher level of resolution). Such distribution of the enormous amount of medical information prevents information overload and ensures that the information is processed accurately and in a timely fashion, and allow medical professionals to receive adequate and accurate information about the patient tailored to the specific setting of the medical care and patient's profile.

Second, this multi-level structure also ensures adaptability of the system, in which the system processes all available data to learn the individual patient's pattern of normal range and abnormal variations. The adaptability is achieved by collecting and processing serial data at the higher scales and then, using this information at the lower scale to individually tailor (edit, adjust) the diagnostic and processing criteria (thresholds). Third, for reasons described above, this multi-level structure also optimizes bi-directional communication and personalized and timely advice and treatment of each patient.

Thus, by vertically distributing the analyses and representation in several levels, the system optimizes information flow, usage of medical knowledge, and improves accuracy of analysis of serial changes, and adaptability to each individual's data. Low, intermediate and high-resolution scales can exchange information between each other for improving the analyses; the scales can be distributed among the units connected by a network and defined according to the corresponding software and hardware resources. In addition, the system can be adapted to optimize usage of medical knowledge contained in medical journals, books, the Internet, and other materials for personalized analysis of serial data. The system optimizes and improves the information flow by vertically distributing it into several levels or Scales according to the importance and relevance of the information, and according to the available software and hardware resources. The low-resolution Scale I represents one-time, periodic, or quasi-periodic snapshot measurements of health data, such as heart rate, blood pressure, blood count, cardiac output, physical activity, temperature, and weight, referred to as the primary elements. The higher-resolution Scale II is used to analyze serial changes in each of these primary elements. Optionally, the $3^{rd}$ scale can be used to analyze combined serial changes of these primary elements. By using this personalized analysis, the system improves accuracy and clarity of analysis and representation of personalized serial analysis. These scales can also include medical knowledge from medical textbooks, journals, and other materials available on the computer network to improve personalized analysis.

Examples of such a multi-scale structure for analysis, representation, distribution and management of health data is presented in FIG. 15. As depicted in the figure, in the first (bottom) scale, data is collected from at least one, and preferably, a multitude of diagnostic devices, such as electrocardiographic, electroencephalographic, echocardiographic, magnetocardiographic, magnetic resonance imaging, computer tomography, thermometer, blood pressure tonometer, pulse oxymeter, impedance meter, genetic/DNA/genotype/proteomics/metabolomics measurements, MRI, CT, ultrasound, fluoroscopic, X-ray image, stress-test, physical activity test, neurographic recordings, biochemical tests, blood tests, enzyme tests, clinical symptoms, such as chest pain, shortness of breath, nausea, etc. These data can be collected as a one-time test, periodic, quasi-periodic, or continuous monitoring (measurements). At the low-resolution level (scale) I, these data are processed to extract the most important indicators (vital signs, diagnostic indicators) or primary elements, such as heart rate, blood pressure, magnitudes and durations of electrocardiographic waves (QRS, T, and P-waves, and ST-segment, T-wave alternans), cardiac output, respiration, temperature, neural activity, etc.

At the next level (scale) II, dynamics of each primary element (vital sign or diagnostic indicator) is analyzed using serial recordings obtained from the individual. The dynamical (serial) analysis is performed using the mathematical, modeling, probabilistic, pattern-recognition, time-series, signal-processing, statistical, computer, and artificial intelligence methods described below. In the simplest-case scenario, serial changes are analyzed using simple statistical parameters, such as the mean or median value, or the standard deviation (a square root of variance), or a range of variations (for example, 25%-75% range) of the time series of serial changes over a certain time interval. The serial changes in any of these statistical parameters or in the combination of these parameters can be estimated, for example, using a statistical test that determines the statistical significance of serial changes over time (for example, a non-parametric, Friedman ANOVA for repeated measurements or a paired t-test, or an ANOVA for repeated measurements), or using pre-selected or adaptive thresholds (for example, a threshold of 3 standard deviations can be used to detect significant changes in the mean values). As a result of this dynamic analysis, trends of changes are represented either as quantitative data, qualitative information, an advice, or graphs of trends in genetic, genomic, proteomic, electrocardiographic, echocardiographic, neurographic (neural), electroencephalographic, magnetocardiographic, magnetoencephalographic, magnetic resonance (MRI), computer tomography (CT) and X-ray imaging. The results of analysis can be also color-coded, for example, if an indicator is within a normal range or within a certain percent of a moving average of previous values, it will be highlighted with a green color. A borderline parameter can be highlighted by yellow color, and a parameter beyond 3 standard deviations from normal range can be highlighted by red color.

The results of dynamic analysis performed at Scale (level) II are sent to the next, third level of processing. They are also sent to the Level I to personalize (adjust, adapt, individually tailor) the diagnostic thresholds. For example, the threshold for detection of tachycardia can be lowered if the subject's individual heart rate during the last several days was slow. Or the threshold for detection of QT-prolongation could be lowered if the subject is taking antriarrhythmic drugs that prolong QT interval.

When the information is transferred to the Level III, dynamics of each vital sign (primary element, diagnostic indicator) is integrated to generate a combined personalized dynamics that includes changes (trends) of various diagnostic indicators. Combining the information or using parameter fusion (when several parameters are combined into a single, composite parameter) improves the diagnostic value of the information, since a combination of parameters can help to achieve a more accurate diagnosis. For example, combination of trends of heart rate and T-wave alternans can be used to determine at which level of heart rate T-wave alternans increase and at which level of heart rate T-wave alternans disappears. Another example is a combined analysis of changes in heart rate and QT-intervals, which allows determining a personalized relationship between these two values. This combined information can be useful for determining an optimal treatment strategy, for example, whether or not the level of T-wave alternans at a given heart rate is abnormal and should be controlled, for example, by implanting an implantable cardioverter-defibrillator (ICD). The results obtained using this combined analysis at Level III are sent to the higher scale and to the lower scales II and I for individual tailoring (personalized adaptation or adjustment) of diagnostic criteria (thresholds).

At Level IV, the results of information processing performed at lower levels I-III are compared with medical knowledge available in medical textbooks, scientific journals, databases, Internet, networks, and libraries, including statistical data, guidelines, and case studies to determine possible diagnoses. The comparison with medical knowledge can be performed using statistical analysis, pattern recognition, artificial intelligence, neural networks, expert systems, mathematical decomposition, mathematical transformation, or mathematical modeling or computer modeling. As a result of this comparison, a list of possible causes of patient's symptoms is determined along with the probability of each diagnosis. This information is sent to the next, Level V, which determines the most probable diagnosis.

Note that the multi-scale (multi-layer) structure can be compressed into fewer (even 2) scales (that can be implemented in the a single microprocessor, computer, cell phone, PDA, smart phone, microcontroller) or expanded into more scales (which can be also distributed among several different parallel or hierarchical databases connected via network or Internet), depending on the specifics of a clinical setup, available hardware and software resources, and depending on the specifics of an individual patient health status and personal profile, including age, diagnosis, disease stage, etc. It is also possible to use any number or combination of the above-described (or similar) levels (layers, scales). For example, a specific diagnostic structure can be used for subjects with chronic congestive heart failure with a typical profile of a low ejection fraction, a low tolerance to physical activity, relatively high resting heart rate and low heart rate variability. Among the parameters that could be modified for such patients is a narrow range of normal heart rate variations. At each scale, the analysis can use at least one of statistical methods, probabilistic methods, Bayesian models/networks, Markov models or hidden Markov models, pattern recognition, artificial intelligence, neural networks, expert systems, mathematical decomposition, mathematical transformation, or mathematical modeling or computer modeling.

FIG. 16 shows another variant of multi-scale structure, in which the 1st level, low-resolution analysis is implemented together with each diagnostic sensor, so that collecting health data and processing these data in a low-resolution, $1^{st}$ level analysis is done at the same place, in a real-time. The collected heath data and/or the results of $1^{st}$-level processing are then sent to the $2^{nd}$ level processing, possibly, via Bluetooth, other radio-transmitters, cell phone, Wi-Fi or other networks. The $2^{nd}$ level processing, as explained earlier, includes analysis of serial changes, using the information obtained previously from the same subject, and sends the results of analysis back to the $1^{st}$ level to optimize diagnostic and monitoring thresholds.

FIG. 17 shows yet another version of a multiscale structure, in which Scale 2 analysis is also distributed among different locations. The 2" scale analysis can be implemented on-site within the same diagnostic unit that collects health data and performs $1^{st}$ scale analysis. Alternatively, the $2^{nd}$ scale analysis can be implemented at a different physical location, or distributed among several different locations, AS FIG. 17 shows.

Note also that the multi-scale structure can be further expanded in horizontal direction, to include different modules of support for different groups of diseases (for example, modules for cardiovascular, neurological, gastroenterological, infectious disease), different patient populations (heart failure, renal failure, chronic obstructive lung disease, elderly, etc.), different groups of medications (anti-arrhythmic, beta-blockers, etc), different device treatments (implantable cardiac devices, hemodialysis, etc.), different medical settings (ambulatory, in-hospital, out-of-hospital, military, mass emergency situations, terrorist threats, weapons of mass destruction alerts).

The multi-scale structure can be implemented in various combinations of computing devices, such as cell phones, specialized processors, personal digital assistant (PDA), smart phone, personal computer, a computer network or specialized networks. It is possible, for example, to implement the first 2 or 3 scales in a miniaturized, personal system (for example, implemented in a cell phone or a personalized monitoring system) that a person carries around, whereas the higher levels are implemented in a computing device that is located remotely and communicates with the lower levels by using wireless communication (cell phone, GPS, GPRS, Internet, Wi-Fi, etc.). Other combinations of scales implemented locally or at remote locations are also possible. Preferably, the higher-level analysis is performed on a powerful computer device, such as a computer server, which has a database of serial data from each subject for comparative analysis, and also a database of medical knowledge of characteristics of different diseases. Another example of implementation of a multi-level structure is a home system, which includes sensors (can be embedded in home appliances, such as bed, chairs); lower and higher-level processing units implemented in a home computer (which can also communicate information to and from an individual via a TV or radio or cell phone) and a higher-level processing (connected via Internet or specialized network) implemented in a medical center. Yet, another example of implementation of a multi-level structure is a car-based system, which includes sensors for physiological monitoring or periodic checkups, (i.e. sensors for monitoring heart rhythm could be incorporated in the armchair; other sensors might be activated and attached to the human body whenever necessary). The sensors are connected with the car's computer (the connection could be wireless, via Bluetooth or Zigbee), so that the computer can perform the scale processing or both, the $1^{st}$ and $2^{nd}$ scale processing. Alternatively, the sensors can communicate directly with a cell phone, which performs the $1^{st}$ or $1^{st}$ and $2^{nd}$ scale processing. The cell phone (or the car computer) can be connected wirelessly (via a cell phone, GPS, or Internet) with a remote computer (which contains a database of this person's serial recordings) for a higher-level processing. Each of these processing levels has a bi-directional communication with other levels for exchanging information, individual tailoring of monitored parameters, providing advice or warnings to the individual in the car or sending an alarm/notification to the individual's physician or nurse via a cell phone or remote computer.

The above-described structure can be used for forecasting (prediction) of the trends in patient's status, including forecasting high-risk periods for developing myocardial ischemia or cardiac arrhythmias by analyzing changes in the pattern of physiological indicators and determining periods when these patterns become unusual (for example, exceeding 3 standard deviations of normal range) or abnormal and, therefore, indicating high-risk of a complication, such as myocardial infarction, arrhythmia, or stroke. The prediction can be performed using at least one of statistical methods, probabilistic methods, Markov models, hidden Markov models, Bayesian network, pattern recognition, artificial intelligence, neural networks, expert systems, mathematical decomposition, mathematical transformation, or mathematical modeling or computer modeling.

The above-described system can be also used to provide an advice or a recommendation regarding changes in diet, stress management, physical activity, treatment (for example, administering a drug or implanting an implantable cardioverter-defibrillator or pacemaker device), or a necessity of diagnostic test. The system can also be used for bi-directional communication between individual subjects (patients), medical centers, and medical professionals (physicians, nurses, and technicians). The above-described system can be also integrated into other information management systems, for example, standard data management systems (such as hospital information management systems developed by Epic Systems, Inc.). The system can represent the results using at least one of quantitative presentation for medical professionals and qualitative presentation for a lay person who has no medical background. Structuring of the analysis is achieved by constructing the at least two, and preferably three, information scales that represent the most significant parameters at different level of detail.

In the practice of this invention, health data is preferably monitored on a substantially continuous, periodic, or quasi-periodic basis, meaning that data are taken or read and recorded periodically such as every few seconds, minutes, hours, days or longer. The periodic recording of data may extend for short periods such as a few minutes or days, or may extend for prolonged periods of time such as weeks, months or longer. The data is generally recorded seriatim or one after another. The data that is recorded may be varied from time-to-time depending on the analysis of data that is collected so as to collect data that may be more relevant to changes in a subject's primary elements. Data is recorded for doing low resolution analysis as well higher scale analyses. As used herein "health data" is used generically to mean all forms of data relating to health, including physiological data that include but are not limited to blood pressure, cardiac output, vascular activity, temperature, respiration, cardiac, abdominal, or breathing sounds, blood flow, hormonal concentration, enzyme and protein levels, genetic, proteomic, metabolomic, and molecular data, neural activity, electroencephalographic activity, and other electrical, mechanic, sonic, biochemical, and biophysical processes in the human body, other information related to human life, including demographic (age, gender), environmental (pollution, job conditions), and psychological data, life styles, exercise activities, etc.

In addition, this invention provides an easy-to-use system for structured and complete analysis and representation of data and its serial changes quantitatively for medical professionals. Structuring of the analysis is achieved by constructing the at least two, and preferably three, information scales that represent the most significant parameters at different level of detail. The multi-scale analysis and representation can be applied to all types of health data defined above. The values of the data obtained from individual patients can be compared with the average values obtained in a group or a population of patients to facilitate analysis of individual data and to determine the values that characterize groups of patients with similar characteristics and/or similar disorders.

A preferred embodiment of this invention further includes implementation of the multi-scale analysis. Specifically, this invention provides for the implementation of the multi-scale analysis on a distributed network of personal devices (which may include devices for registration and processing of electrocardiogram, electroencephalogram, blood pressure, cardiac output, temperature, respiration, vascular tone, blood glucose, and other biochemical, biophysical, biomechanical, hormonal, molecular, and genetic data) and centralized computers with a bi-directional communication between them. This distributed network allows: 1) uninterrupted data acquisition (continuous or discrete) anytime, anywhere, 2) fast transmission of the acquired information to the other computers on the network for processing and comparison with previously acquired serial data (including individual baseline data), 3) fast and accurate processing, analysis, and accurate detection of serial changes, 4) transmitting the results back to personal devices (held by the individuals and medical personnel) to inform them and adjust the monitoring thresholds.

On the network, the data and its processing may be distributed horizontally among the devices and computers according to the computational resources, time period of data acquisition, type(s) of a medical test(s), geographical location, professional and living environment. For example, one distributed personal network of devices and computers could be setup at home, a second network could be setup at a work place, a third network could be setup in a hospital, and a fourth one could be setup in a transportation system (such as a train or an airplane), so that all four networks are connected to each other and can exchange the information instantly. The personal devices may include devices for acquisition and analysis of electrocardiogram, electroencephalogram, electromyogram, blood pressure, impedance, vascular resistance, cardiac output, biochemical, genetic, proteomic, molecular, and other types of health and environmental data.

The advantages of the distributed processing include: 1) a higher computational power and speed of distributed parallel processing, which allow efficient implementation of such computationally expensive methods of artificial intelligence as neural networks, expert systems, and hybrid artificial intelligence systems, and other mathematical and statistical tools, and 2) fast exchange of information among the devices on the network as well as between different networks.

Low, intermediate and high-resolution scales are defined according to the corresponding software and hardware resources. A low-resolution (Scale I) represents a small number of the most important primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each physiological signal utilizing computational resources of intermediate or high-resolution levels. At the intermediate-resolution (Scale II), serial changes in each of the said elements are determined using a mathematical decomposition into series of orthogonal basis functions and their coefficients. This scale is implemented using a specialized processor or a computer organizer. At the high-resolution (Scale III), serial changes in all elements of the ECG and their combinations are extracted using orthogonal mathematical decomposition to provide complete information about the dynamics of the signal. This scale is implemented using a powerful processor, a network of computers or the Internet. Scale I may be implemented in a portable, pocket-size device, in which the signal is decomposed into a plurality of primary elements and parameters such as intervals between the heart beats, type of a cardiac complex, amplitudes and duration of P-, QRS, T-, and U-wave, QT-interval, amplitude of ST-segment. Scale I of the system provides the means for real-time electrocardiographic analysis by comparing the primary elements of ECG with reference values (individual thresholds) using the minimum computational resources. The reference values are programmed into the device based on normal values for the primary elements for the patient. Scale I includes means for adjustment of individual thresholds and criteria for rejection of noisy data. A detector of noise and error rejects the noisy data if the primary elements exceed physiologic range. Alternatively, modification of the primary elements and adjustment of their search criteria can be performed automatically at the higher-resolution Scale II or Scale III. In this case, the Scale I analysis is implemented using a programmable microprocessor that can be re-programmed at the higher-resolution scales to account for the individual characteristics of the physiological pattern and monitoring goals. Specific sets of primary elements can be used for patients with different cardiovascular abnormalities.

Scale I can be used in two modes: static mode and dynamic mode. The static mode is used for one-time ECG examination in which the newly acquired primary elements are compared with the default reference values. The dynamic mode is used for comparison of the newly acquired primary elements and waveforms with the primary elements and waveforms that were previously acquired from the same person. The shapes of QRS, T, and P-waves are compared using cross-correlation function. A small magnitude of the difference between the two measurements permits classifying them as substantially similar and keeping only one measurement in the memory.

Scale I provides sufficient information for standard, one-time, clinical ECG examination. The most significant primary elements may be represented as a color, symbol, or other easy-to-read encoding of indicators that make the results useful and understandable for a lay person and a medical professional. Each signal-indicator corresponds to a single primary element. In the static mode, the values of the indicators are preferably color-coded for a lay person into normal, moderately or severely abnormal. This representation constitutes a static screen. Alternatively, the indicators may be symbol-coded, N for normal and A for abnormal reading; or they may vibrate or produce a sound output for people with vision or hearing impairments. For a medical professional, the indicators provide exact, quantitative values of the primary elements. In the dynamic mode, the indicators are preferably symbol (or color)-coded into C for changed or U for unchanged. This representation constitutes a dynamic screen.

Intermediate-resolution Scale II allows viewing the ECG with automatically determined primary elements on a display and interactive editing of the set of primary elements and their search criteria. The editing can be performed by a user or a medical professional to modify the set of characteristic points or to adjust their search criteria, and can be performed either manually or automatically by the software. The individually adjusted search criteria can then be used to re-program the Scale I analysis as described earlier.

Scale II allows accurate comparison of serial ECGs and detection of small serial changes that may be unexposed by visual inspection of the signals. This scale requires higher computational resources than Scale I and can be implemented in a specialized processor, computer organizer or a personal computer. These computational resources also allow manual entering text information about the patient into the database and specific instructions regarding adjustment of time windows, threshold values, and other variables. To perform the Scale II analysis, the primary elements from serial ECGs are stored into a database to construct the time series for each primary element. The series is decomposed into a few most significant basis functions and coefficients using Principal Component Analysis (PCA) or any other orthogonal set of basis functions. The newly acquired values of the primary elements are compared with the series of the previously obtained values. Furthermore, the changes in the series of PCA coefficients are analyzed to detect small cumulative changes in the dynamics of the series that indicate instability in the cardiac electrical activity.

High-resolution Scale III is used to analyze individual and combined changes in the primary elements; at this scale, the number of the primary variables is increased to include the entire waveform of the cardiac complexes. This allows the most sensitive and accurate detection of the small changes in the individual electrocardiographic pattern. The same PCA approach is used at this scale to expose small serial changes in the ECG recordings. Scale III requires higher computational resources compared to Scale I and Scale II; it may be implemented in a powerful processing unit such as a personal or specialized computer or a distributed network of computers or the Internet.

This invention can be used for one-time examinations by patients, medical professionals, paramedics and lay public, and for dynamic assessment of changes in cardiac electrical activity. The information can be transmitted to an external computer system or a network of computers. For a lay person, the system may also include a database explaining significance of the changes in each primary element and providing simple recommendations about the measures that has to be taken if the readings of the indicators become abnormal. These may include complete cessation of physical activity, contacting a medical professional, taking a medication, etc. More detailed recommendations might be provided for patients who have specific abnormalities or medications. These patients might require special monitoring or individual adjustment of their primary elements. For example, specific monitoring the duration of QT-interval is important in patients taking antiarrhythmic drugs that prolong QT-interval.

The system can be used as:

Hospital or medical center information management;
Information management for ambulatory patients;
Information management for community health program;
Information management for corporate health program;
Self-awareness and health advice system;
Information management for patients with implantable devices;
Medical decision support system for medical professionals implemented on a personal computer, a cell phone, a smart phone, or a personal digital assistant (PDA);
Information management or decision support system that includes personalized analysis of serial data and medical knowledge contained in medical literature and on the Internet;
Personalized advice system implemented on a personal computer, a cell phone, a smart phone, or a personal digital assistant (PDA);
First-aid health-data analyzer for emergency units, paramedics, and medical personnel;
Health data analyzer for a routine medical examination;
A personal one-time or serial data analyzer with storage of individual historic data, adaptive adjustment of individual thresholds and assessment of changes in individual heath pattern;
A one-time or serial health-data analyzer for a group of people, a family or a patient group, with storage of individual historic data for each person, adjustment of individual thresholds and assessment of changes in individual health patterns;
Event-monitoring device including patient-detected events;
Bedside monitoring;
Bedside or ambulatory monitoring providing intelligent alarms to medical professionals when appropriate;
At least one of arrhythmia, stress-test, ischemia, ST-segment, and T-wave alternans monitoring;
Pacemaker and other implantable device checking, bi-directional or uni-directional communication, programming, and control;
Evaluation of the treatment efficacy, side effects and progression of the disease.

Accordingly, an object of this invention is to provide a system for analyzing ECG signals at least at two levels of detail or resolution. Both levels of resolution are presented in simple representation that can be understood by lay persons, as well as medical professionals.

A further object of this invention is to provide an ECG analyzing system that includes a monitoring device for receiving and analyzing ECG signals and which includes means for communicating with an external computer to which the ECG signals can be forwarded for more complex analysis. The monitoring device can be reprogrammed by the external computer to select the primary elements of the ECG signals that are unstable or abnormal. The low level analysis performed by the monitoring device is thus focused on the critical primary elements for that patient.

The system of the present invention can be used for management and analysis of electronic health (medical) records and information, analysis and management of biometric data, or information management of other types of healthcare data.

The system of the present invention provides instant access to information from a variety of distributed sources to reduce costs, improve quality of patient care and optimize decision making. For example, the system can be used to provide a real-time view of in-hospital patient distribution and operations structure in different departments and at different stages of the treatment process, from admission to discharge, or in the Emergency Room. The system can capture and integrate monitoring of vital signs, biometrical data, capture and integrate text, images, technical information related to device functioning and instrumentation status. The system can also provide an intelligent, tailored representation for different types of users and different points of care. For example, it can improve information sharing among the healthcare providers, including physicians, nurses, technicians, clerks, and others. The system of the present invention can also facilitate analysis, management, and optimization of information processing from the traditional departmental systems—e.g., legacy systems (Nursing, Pharmacy, LIS, RIS, PAS, by creating integrated database, applying intelligent analysis and optimizing diagnosis and treatment, including diagnostic and treatment plans and providing intelligent alarms and alerts to support and optimize clinical decision making.

The system of the present invention can collect real-time physiological and health data from a variety of sensors including vital sign monitors, ventilators, infusion pumps. It can also support a wide range of physiologic sensors from a variety of manufacturers. The system can also automatically re-configure itself to accept and recognize new data from physiological sensors whenever a new sensor is plugged into the system. It is also possible to enter new data into the system using an integrated barcode scanning or RFID tag or MEMS tag or other types of automatic entry of information at the bedside in a real time. The system of the present invention can also adapt, compare and merge new information with the data that already exist in the system. Because the information flow between different levels/units of the system is bi-directional, the system supports and optimizes seamless exchange of data coming from different diagnostic and treatment modalities, such as patient information from hospital data repositories (e.g., Laboratory, Medication, Admission/Discharge/Transfer and others) and intelligently alert the clinician to potential problems.

The system can also have multiple displays, terminals, including wireless connections with personal handheld devices (PDA, Smart Phones, Cell phones, computers, and computer tablets). Using these displays, users can simultaneously receive different modes of information, such as physiological signal information (vital signs, ECG, blood pressure, cardiac output), real-time intelligent alerts, prescription dispensing, drug interaction, dynamical report, individual patient dynamics, and serial comparison of individual patient's data, etc.

For example, an acute ischemic syndrome (AIS) can be confirmed by measurements of the level of cardiac enzymes (troponins). Since the level of enzymes can be estimated only in a hospital, this information is usually unavailable when the subject is admitted to the emergency room. In the absence of this information, medical decision is made on the analysis of clinical and electrocardiographic signs of ischemia. Yet, this information is incomplete. Thus, the information completeness is estimated relative to the total, theoretically possible, information about a disease state (which is equal to 1), so that the sum of information content (probability estimates, or uncertainty) of all diagnostic tests is equal to 1. The information contained in each test is equal to a number between 0 and 1. At each scale the information completeness (probability of each disease state) can be estimated relative to the complete information (reference) for this disease state. Similarly, the information completeness is also estimated for all scales, relative to the complete, theoretically possible information in all scales.

The probability or information completeness can be represented by the probability transition matrix of a Markov chain, Bayesian probability, probabilistic neural network, or some other non-probabilistic matrices and methods.

Traditionally, the term "multiscale analysis" or "multi-resolution analysis" refers to either (1) a spatial multiscale analysis (distributing analysis of complex structures or processes that span different spatial scales, for example, molecular-cellular-organ-body scales of biological processes into several spatial scales), or (2) a temporal multiscale analysis (distributing analysis of complex, dynamic processes that involve several different time-scales). The term multiscale analysis used herein refers to the temporal multiscale analysis adapted to serial (longitudinal) data or a combination of temporal and structural multiscale analysis adapted to serial (longitudinal) data (because serial images, image information, and other data spanning different spatial scales can be also included in the analysis). Note that the traditional temporal multiscale analysis refers to an application of a mathematical formula or function (for example, a wavelet function or a nonlinear function, such as entropy), to different time-scales by varying a time-window parameter (i.e. using a mathematical translation or dilation of a function). A detailed description of a multiscale wavelet analysis can be found in The Statistician (2000) 49, Part 1, pp. 1-29 (Abramovich F, Bailey T C, Sapatinas T. Wavelet analysis and its statistical applications.). A description of a multiscale entropy analysis can be found in Physical Review E 71, 2005, pp. 021 9061-021 9061 8 (Costa, M, Goldberger A L, Peng, C.-K. Multiscale entropy analysis of biological signals). In this approach, the fundamental mathematical function remains unchanged at all time scales, but the scaling parameters change. Our multiscale approach, presented herein and in our previous Applications (application Ser. No. 10/816,638, filed Apr. 2, 2004, which is a continuation-in-part of application Ser. No. 10/124,651, filed Apr. 17, 2002, now U.S. Pat. No. 6,925,324, which was a continuation-in-part of application Ser. No. 09/583,668, filed May 30, 2000, now U.S. Pat. No. 6,389,308), incorporated herein by reference, is different from the traditional methods for multiscale analysis described above (in some respects, it can be viewed as a non-trivial generalization of the traditional multiscale and multi-resolution approaches). It allows 1) usage of different mathematical, pattern-recognition, statistical, probabilistic, artificial-intelligence functions/models/estimates/approximations at different time scales, 2) usage of a single time-point (snapshot) compared against reference values at the $1^{st}$ scale of analysis (this snapshot analysis can be performed one-time, periodically, quasi-periodically, or continuously) and multiple time-points (serial data) at the higher-scales of analysis, 3) usage of composite functions and estimates obtained by combining different parameters and time-scales at higher-level analytical scales, 4) bi-directional exchange of information between different scales to improve the analysis. Using recently introduced terminology, our multiscale analysis approach can also be viewed as a non-trivial extension, improvement, and generalization of a recursive projection method (Shroff G M, Keller H B. (1993) *SIAM J. Numer. Anal.* 30, 1099-1120) that can be also adapted for "equation-free modeling" (Theodoropoulos C, Qian Y-H, Kevrekidis I G. *PNAS* (2000) 97, 9840-9843) of multiscale, complex processes.

The above and other objects and advantages of this invention will be more fully understood and appreciated by reference to the following description and the drawings.

BRIEF DESCRIPTION OF THE DRAWINGS

A full understanding of the invention can be gained from the following description of the preferred embodiments when read in conjunction with the accompanying drawings in which:

FIG. 3 shows the set of indicators that represent the results of ECG analysis at Scale I both qualitatively and quantitatively in a static mode ("N" denotes normal value and "A" denotes an abnormal value of a characteristic parameter).

FIG. 4 shows the set of output indicators that represent the results of ECG analysis at Scale I both qualitatively and quantitatively in a dynamic mode ("U" represents unchanged value and "C" represents a changed value of a characteristic parameter compared to a previous recording).

FIG. 8 shows the readings from the output indicators at Scale I in the static mode for the abnormal ECG in FIG. 6 (N denotes a normal value, A denotes an abnormal value of a characteristic parameter compared to default values).

FIG. 10 shows the readings from the indicators at Scale I in the dynamic mode for the abnormal ECG in FIG. 9.

DESCRIPTION OF THE PREFERRED EMBODIMENTS

Figure 1:
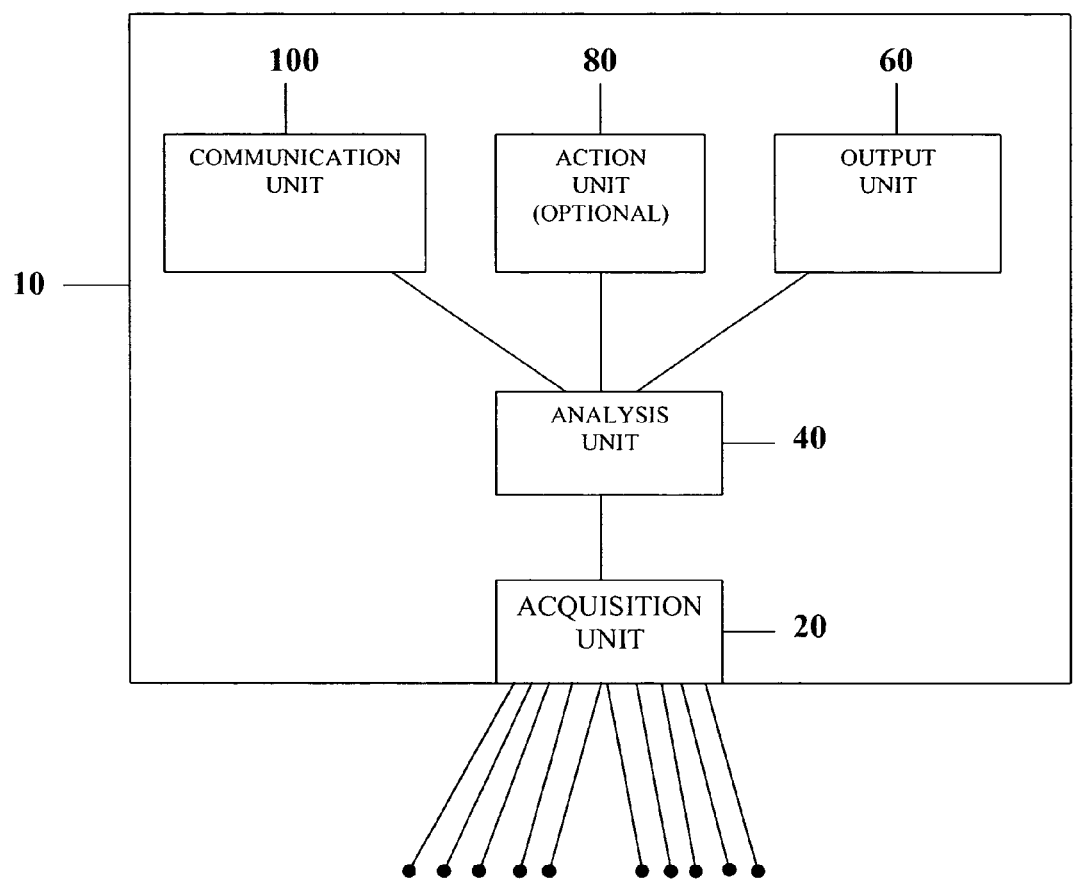
FIG. 1 is a block diagram of the multi-scale (multi-resolution, multi-level, multi-layer) method and system of the preferred embodiment of this invention.
Figure 2:
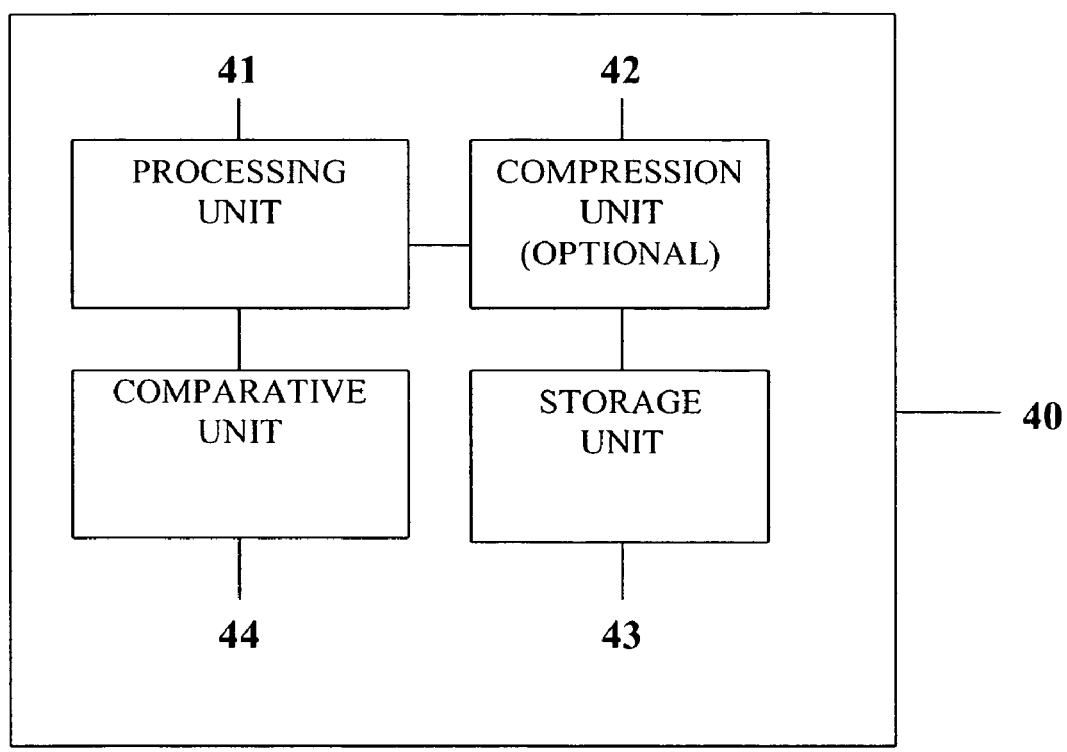
FIG. 2 is a block diagram of the analysis unit of a physiological monitoring system (for example, an electrocardiographic, ECG system), which is interfaced with the first level of the system of the present invention (to incorporate the ECG data, processed or unprocessed), as shown in FIG. 1, bottom level.

FIG. 1 is a block-diagram of a preferred embodiment of a system for at least one of information management, decision support, diagnosis, examination (physical, physiological, biochemical, etc.), monitoring, advice, medical recommendation, and bi-directional communication between individuals (patients), medical professionals (physicians, nurses, technicians) and medical centers. The system may receive physiological or health data (for example, ECG data) from a recorded data source for analysis, but preferably receives the data real-time, on-line. As used herein, patient means an animal, and most likely a human. The medical device further includes an analysis unit or module 40 which, in turn, consists of processing, compression, storage, and comparison units (FIG. 2). The processing unit 41 can be a typical computer or personal computer of the type available from many vendors such as IBM and Hewlett-Packard. The processing unit 41 is programmed to detect a plurality of characteristic points such as the onset, peak and offset of P-, Q-, R-, S-, T-, U-waves, and computes the characteristic parameters or primary elements which include amplitudes of the said waves and ST-segment, duration of PQ-, QRS-, and QT-intervals. The processing unit 41 has a programmable microprocessor that can be programmed to modify or change the set of primary elements or to adjust their search criteria. This allows individual adjustment of the characteristic points which, in turn, increases the accuracy of detection of the primary elements. For instance, in signals with biphasic T-wave, two T-peaks should be detected, whereas monophasic T-wave requires detection of a single T-peak. Furthermore, the criteria for determining the offset of biphasic T-wave are different from the criteria for the offset of monophasic T-wave. Individual adjustment of the primary elements and their search criteria increases the accuracy of the detection of characteristic points in different ECG patterns. Still another possibility is analysis of combined changes in some primary elements or disabling analysis of the other elements. For example, in patients with possible electrolyte abnormalities, the amplitudes of the T-wave and U-wave may be combined into a single index which will be convenient for monitoring. Furthermore, the set of monitored primary elements can be modified according to the specifics of cardiovascular abnormality. For example, in patients with coronary artery disease, the amplitude and the slope of the ST-segment should be monitored continuously.

Compression unit 42 compresses the ECG waveform into a few weighted basis vectors and their coefficients using principal component analysis, wavelet decomposition, or other orthogonal mathematical transformation. Storage unit 43 stores the compressed waveforms and the computed primary elements into memory. Comparative unit 44 compares the newly acquired waveforms and newly computed primary elements with the waveforms and primary elements previously stored in the storage unit 43. The analysis unit 40 has means for adjusting the thresholds for each indicator, whereas the default values correspond to normal ECG. An output unit 60 includes a screen or a set of indicators for displaying the ECG waveforms and the computed primary elements in comparison with the previously stored primary elements or in comparison with the default reference values. The results of comparison can be represented both qualitatively and quantitatively in the dynamic and static modes. In the static mode, the quantitative representation includes exact values of the primary elements and the type of the cardiac complexes, whereas the qualitative representation includes indication of each parameter as being normal (N) or abnormal (A) as shown in FIG. 3. Abnormal readings may be further classified into moderately abnormal and severely abnormal. To make the indicators understandable to a lay person, the degree of abnormality may be color-coded: green color corresponds to a normal value, yellow corresponds to a moderate abnormality, and red corresponds to a severe abnormality. In the dynamic mode, the quantitative representation shows the differences between the newly acquired and stored primary elements and waveforms, whereas the qualitative representation includes indication of each parameter as being changed (C) or unchanged (U) as shown in FIG. 4. The output unit 60 may alternatively or additionally feed an output data to an action unit 80 for sounding an alarm, generating a vibration, or taking appropriate measures, such as applying the drugs or adjusting the therapy mode. Communication unit 100 transmits the information between the device 10 and external higher-level processing device 150. The communication unit 100 may be a modem or a wireless transmitter/receiver. Electrocardiographic signals and recorded values of primary elements and indexes are transmitted from the device 10 to higher level devices for more detailed processing and storage. The higher-level device 110 preferably transmits back to device 10 a set of primary elements and their search criteria to be used in device 10.

Figure 5:
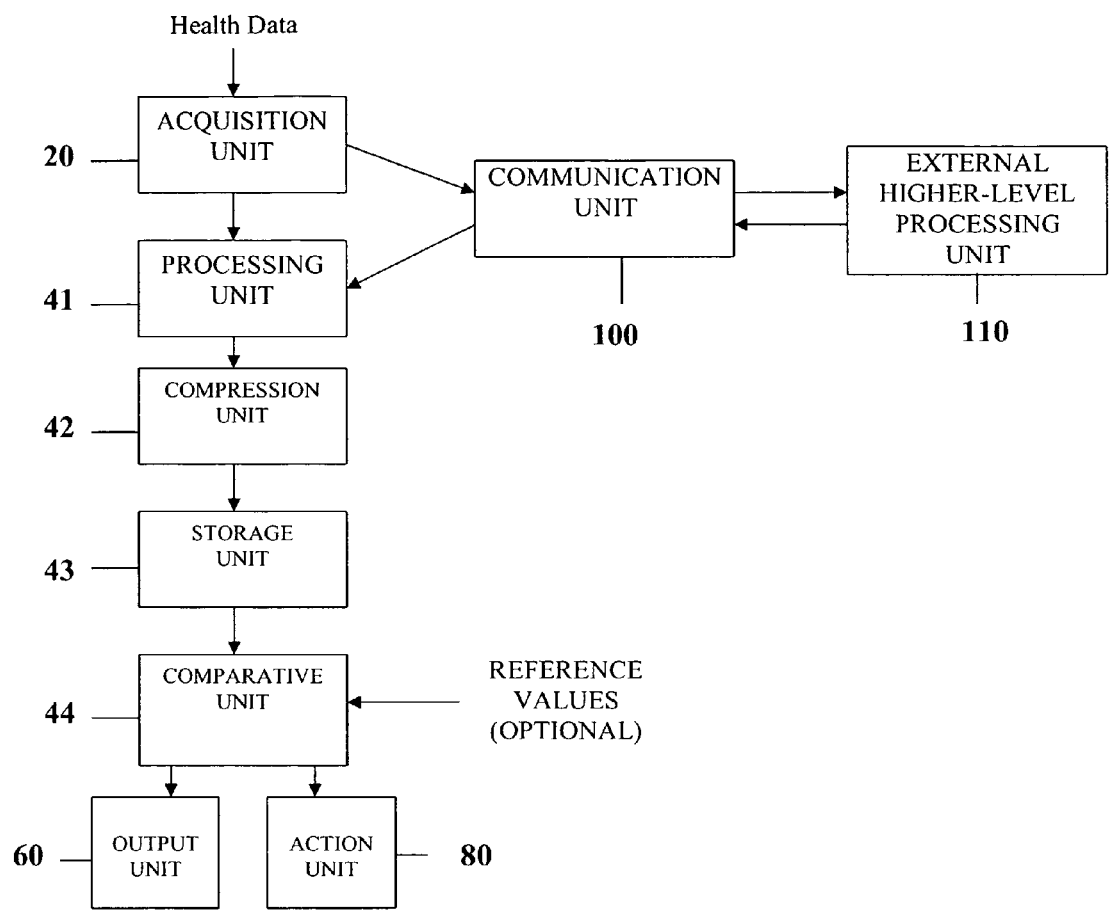
FIG. 5 is a flowchart of operation of the preferred embodiment.

FIG. 5 is a flow-chart of operation of this medical device.

Figure 6:
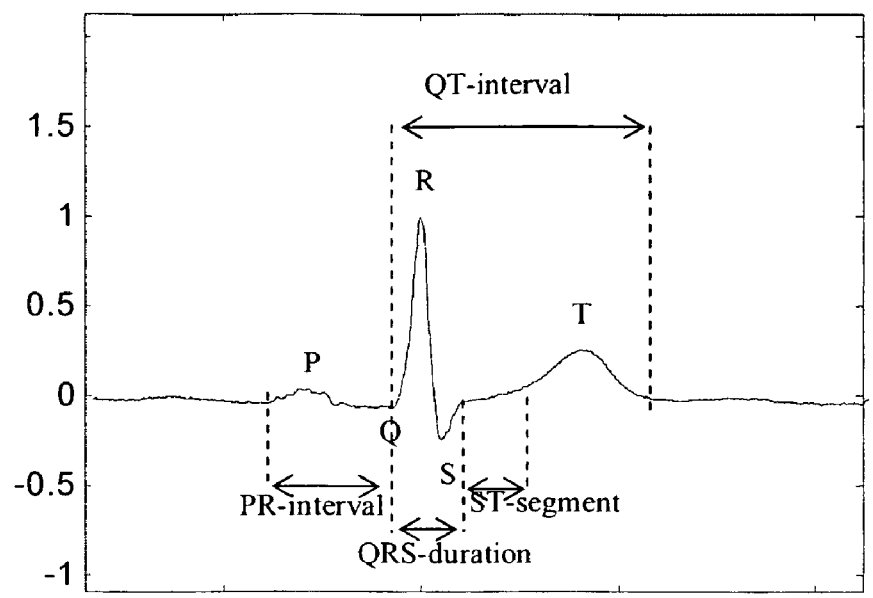
FIG. 6 is a graph of a representative electrocardiogram from a normal subject and its segmentation into a plurality of characteristic points and segments.

FIG. 6 shows a representative ECG obtained from a normal subject and position of the characteristic points in the signal.

To achieve the optimal sensitivity in the detection of hidden or small ECG changes, a pattern recognition approach is used that extracts the basis functions from the statistics of the signal itself and gives the least error representation of the signal. Specifically, a principal component analysis (PCA) is applied which requires a minimum number of basis functions to obtain a fixed reconstruction error compared to other orthogonal expansions.

PCA is an orthogonal transformation that employs a weighted combination of several basis functions to represent a signal. The basis functions are fixed, whereas PCA-coefficients vary as a function of time. The choice of PCA for detection and characterization of the changes in ECG-signal was related to the following properties of the transform:

minimization of the mean square error within a finite number of basis functions guarantees that no other expansion will give a lower approximation error (with respect to the mean square error).

clustering transformational properties with minimization of the entropy in terms of the average squared coefficients used in the expansion.

In contrast to the methods that use fixed-form basis functions (for example, Fourier representation), basis functions in PCA are derived from the statistics of the signal. Therefore, PCA with the same number of basis functions provides a smaller residual error than other expansions.

Assume that the pattern contains M vectors $x_i$, i=1, 2, ..., M, and the length of each vector is equal to N points. To obtain the PCA coefficients, the matrix $C_x$ must be obtained using the average of the covariance matrices of x vectors. The matrix $C_x$ is defined as $$C_x = E\{(x-m_x)(x-m_x)^T\} \quad (1)$$

where $$m_x = E\{x\} \quad (2)$$

is the mean vector, and E corresponds to the expected value. Assume that the pattern of the time series has M unit-length vectors $x_i$, i=1, 2, ..., M, and the length of each vector is equal to N points, to generate a matrix $C_x$ from the outer products of vectors x. A matrix $C_x$ of M vectors $x_i$ can be calculated as $$C_x \cong \frac{1}{M} \sum_{i=1}^{M} \{(x_i - \hat{m}_x)(x_i - \hat{m}_x)^T\}, \quad (3)$$

where i = 1, 2, ... M, and $$\hat{m}_x \cong \frac{1}{M} \sum_{i=1}^{M} x_i \quad (4)$$

From the matrix $C_x$ one can obtain eigenvectors $\psi_i$, i=1, 2, ..., N and corresponding eigenvalues $\lambda_i$, i=1, 2, ..., N. Let A be the transformation matrix whose rows are the eigenvectors of $C_x$. First eigenvector corresponds to the first eigenvalue, second one corresponds to the second eigenvalue and so on. Eigenvalues are arranged in decreasing order so that $\lambda_1 \geq \lambda_2 \geq ... \geq \lambda_N$. Then, PCA consists of a multiplication of the transformation matrix A by vector $(x-m_x)$:

$$y = A(x-m_x) \quad (5)$$

where y is a PCA coefficient vector. If matrix A is formed by K eigenvectors that correspond to the largest eigenvalues, y is a K×1 vector. Then, the first K coefficients contain almost entire information about the signal allowing substantial reduction in the number of analyzed coefficients and thus compression of the data. In this application, PCA is applied to the time series of each primary element, that is the intervals between the cardiac beats, duration of PQ, QRS, and QT-intervals, amplitudes of P-, Q-, R-, S-, and T-waves. For instance, to determine the characteristic pattern of the series of QT-intervals from the serial ECGs, assume that the pattern consists of M unit-length vectors $x_i$. Therefore, the series is divided into M constant-length time windows to obtain vectors $x_i$. Alternatively, the unit-length vectors x, may be comprised of a combination of all or some primary elements to determine a typical combinatorial pattern of the primary elements. Still another possibility is an extension of the concept of the unit-length vectors x, into two dimensions to represent both the combined pattern of all primary elements (in the first dimension) and the serial changes of each primary element (in the second dimension). Then PCA analysis is performed as described above.

Applications of Mathematical Transformations at Scale II and Scale III of the System The analysis described hereafter could be used as a stand-alone tool or a part of an integrated processing and analytical system, such as an artificial intelligence system, which includes neural networks and expert systems. The analysis could be performed on a single computer or a distributed computer network, possibly, with parallel processing. In previous works, mathematical transformations, and in particular, the principal component analysis (PCA) was applied for detection and classification of cardiac waveforms (QRS-complexes and ST-segments) in ECG. The optimal basis functions for QRS or ST waveforms were obtained from large training sets. PCA coefficients were used to compare individual waveforms with the set of templates and to assign the waveform to one of the classes.

Instead of applying PCA to the signal as in the previous art studies, this invention preferably applies PCA to the time series of primary elements that are extracted from the ECG-signal. This modification provides the following advantages. First, this provides an objective and accurate estimation of the serial changes in the ECG-signals and reveals small or hidden abnormalities that cannot be exposed by the previously used techniques. Second, this allows dramatic compression of the data. Third, this analysis reveals independent changes in each primary element when simultaneous changes occur in several elements. The prior art analysis of the original ECG signal might not show any changes because of the cancellation effects between the elements undergoing changes in opposite directions.

Because the time series of primary elements is nonstationary and highly variable among subjects and in the same subject over different periods of time, typical waveforms or templates of this series cannot be determined. Therefore, temporal, adaptive changes in PCA coefficients are used to detect and characterize the changes in this series. Pronounced and complex changes in the series of primary elements are identified by the simultaneous changes in several PCA coefficients. Since the basis functions in this expansion are orthogonal, simultaneous changes in several coefficients represent complex disturbances in linearly independent components of the signal. These combined changes in PCA coefficients reveal serious instabilities in the cardiac function as shown in the following examples.

The signal is separated into consecutive windows, and an array of vectors is obtained from the series. A covariance matrix is formed by the formula (3), where M is the number of vectors, $x_i$ is $i^{th}$ vector, and $m_x$ is calculated as in formula (4). Basis functions or eigenvectors are obtained from this matrix. Since only one covariance N×N matrix (N is the window length) is generated from the signal, all eigenvectors are fixed.

Example I

The following example illustrates the sequence of ECG analysis at the system's Scales I, II and III. Serial ECG recordings from a patient A who had a structural heart disease and dynamic changes in the electrocardiogram were processed at each Scale with a different degree of detail. Scale I revealed the changes in a small number of important, primary elements using minimum computational resources. Scale II exposed changes in the primary elements that occurred in serial recordings over time. Scale III provided complete description of the serial ECG changes using a complete set of primary elements and their combinations.

System Initialization.

Figure 7:
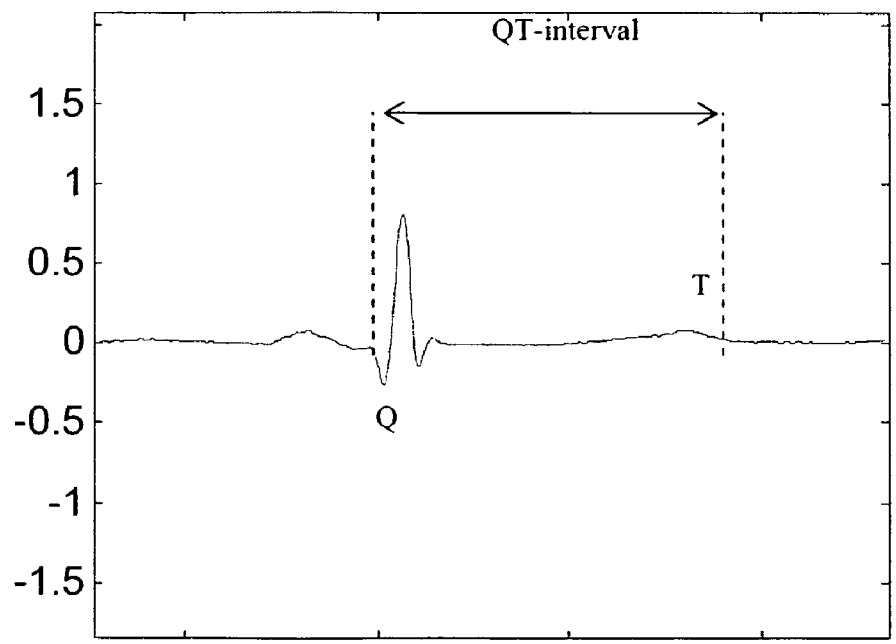
FIG. 7 is a graph of a representative electrocardiogram from a patient with a cardiac disease, large Q-wave, and prolonged QT-interval (0.5 sec) compared to the normal ECG shown in FIG. 6.

When the system is used for the first time, initialization is required for verification and individual adjustment of the analysis criteria including identification of the primary elements and their search criteria. System initialization is performed using the hardware and software resources of the intermediate resolution Scale II and high resolution Scale III. In the initialization mode, the Scale I device transmits ECG to the higher Scale of the system via a direct or a wireless (telemetry or infrared) link. The ECG and the position of primary elements and their characteristic points (onset, peak, and offset) are visualized on a display, for example LCD display, as shown in FIG. 6. The position of characteristic points can be verified and manually edited by a user, a lay person or a medical professional. A simple manual or a software tutoring program of the typical ECG patterns, the primary elements and their characteristic points is provided for a lay person. FIG. 7 shows an ECG with a long QT-interval (0.5 sec) and a low-amplitude T-wave compared to the normal ECG shown in FIG. 6. The offset of this low-amplitude T-wave is difficult to detect automatically and a manual verification and correction are desired to ensure the accuracy. A user may also modify the set of monitored primary elements to account for a specific cardiovascular abnormality. Some of the elements may be combined into a single monitoring index, for example, a combined integral of T and U peaks can be useful for patients with possible electrolyte abnormalities.

After finishing manual verification and editing, the system automatically adjusts the search criteria for each characteristic point which include the time window, the amplitude, integral and derivative thresholds. The individually adjusted program is generated for a particular person and is automatically sent to re-program the processing sub-unit of Scale I. After the initialization, the Scale I device can work in autonomous regime without permanent connection to the higher-level Scales.

Re-initialization and serial adjustment can be performed to modify the set of primary elements and indexes and their search criteria. In addition to the procedure that was described in the system initialization, the results of the Scale II analysis can be used for serial adjustment. In particular, the primary elements and indexes whose time series and PCA coefficients demonstrate unstable behavior can be identified and included into the Scale I analysis.

Figure 9:
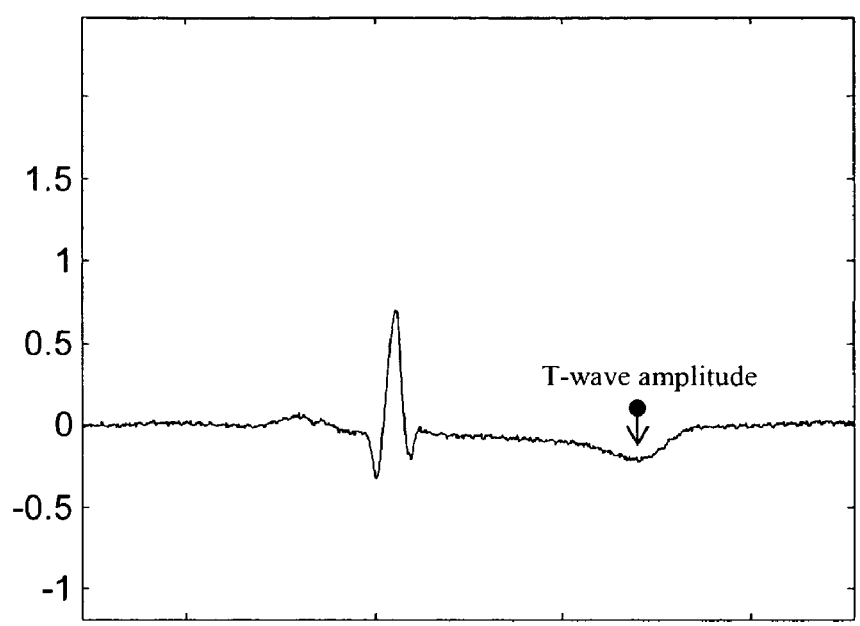
FIG. 9 is a graph of ECG obtained from the same patient as in FIG. 8 several hours later. The amplitude of T-wave decreased by 0.3 mV compared to the previous recording shown in FIG. 7.

Scale I. FIG. 7 is a graph of a representative electrocardiogram which has large Q-wave, and prolonged QT-interval. These abnormalities have been detected by the method of the present invention at the Scale I and represented qualitatively as abnormal findings and quantitatively as the exact magnitude of changes compared to the default values as shown in FIG. 8 which are readings of output indicators at Scale I for abnormal (A) and normal (N) ECG in the static mode. FIG. 9 is a graph of ECG obtained from the same patient several hours later. The amplitude of T-wave decreased by 0.3 mV compared to the previous recording shown in FIG. 8. The amplitude of T-wave decreased by 0.3 mV compared to the previous recording shown in FIG. 7. FIG. 9 shows the readings from the output indicators that represent the changes (C) in this ECG compared to the previous one.

Figure 11:
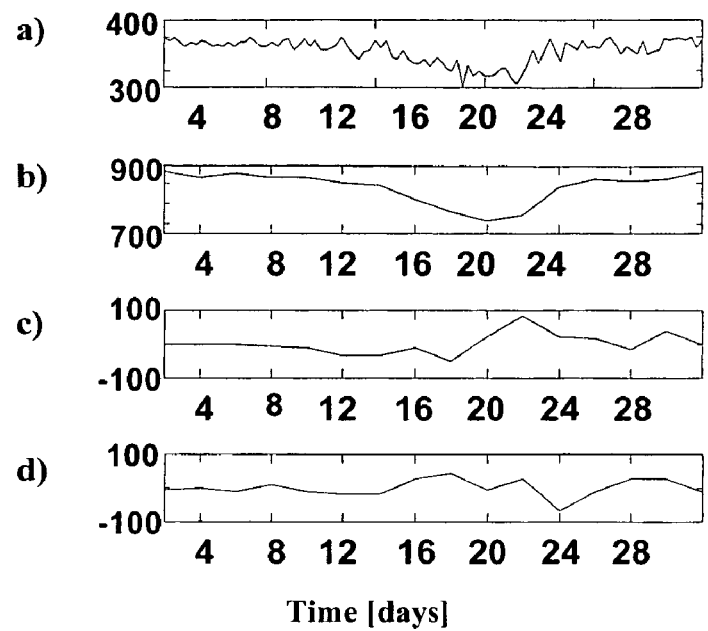
FIG. 11 shows the time series of QT-intervals (panel A) and its first three PCA-coefficients (panels B-D) in patient A during one month.
Figure 12:
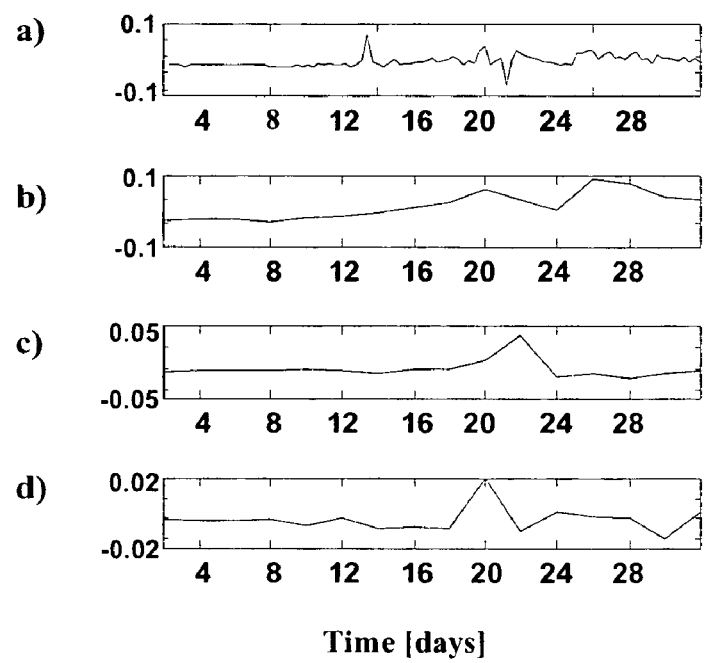
FIG. 12 shows the time series of ST-segment and T-wave amplitudes (panel A) and its first three PCA-coefficients (panels B-D) in patient A during one month.

Scale II. Serial ECGs have been obtained from patient A. and processed by means of Scale II to expose the time course of the serial changes that occurred in the this patient over a period of 1 month. FIG. 11, panel a, represents the series of QT-intervals that were extracted from these recordings; panels b-d demonstrate the changes in the first three PCA-coefficients that were obtained from this signal. At the end of the last recording, the patient developed a life-threatening disorder of cardiac function. However, this method reveals instability in the cardiac function as early as 20 days before the event when all known physiological indicators remain normal. FIG. 12 demonstrates changes in the ST-segment and T-wave amplitude extracted from the same recordings (panel a) and the corresponding first three PCA-coefficients. The time series are complex and the changes cannot be easily described or analyzed by simple tools, therefore, the changes in the signal are analyzed in a compressed form using the series of the first three PCA-coefficients which contain the most significant information about the signal. The ECG was relatively stable during the first 10 days but then became unstable as reflected by variations in the PCA-coefficients. The patient suffered a life-threatening cardiac disorder at the end of the month. However, variations in the PCA-coefficients were observed long before the event, when all physiological indicators remained normal. Calculating the changes in the variance of the PCA coefficients provides an accurate estimation of the changes and stability of the series. Unlike linear estimators such as the mean and variance of the signal or nonlinear estimators such as fractal scaling exponent or correlation dimension, disturbances in the PCA coefficients are indicative of any changes in the pattern of the signal. Therefore, analysis of PCA coefficients reveals both linear and nonlinear changes in the signal.

Figure 13:
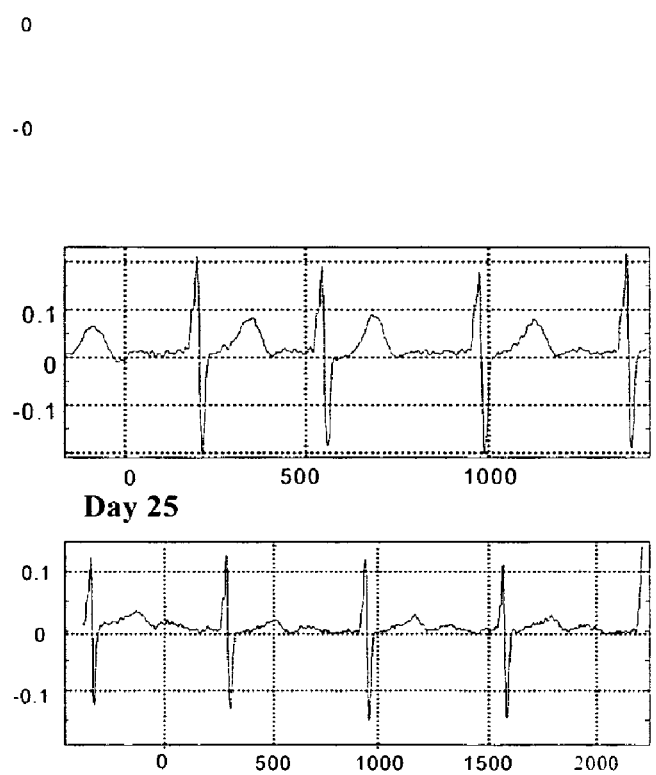
FIG. 13 shows serial ECG tracings of patient A during one month.
Figure 15:
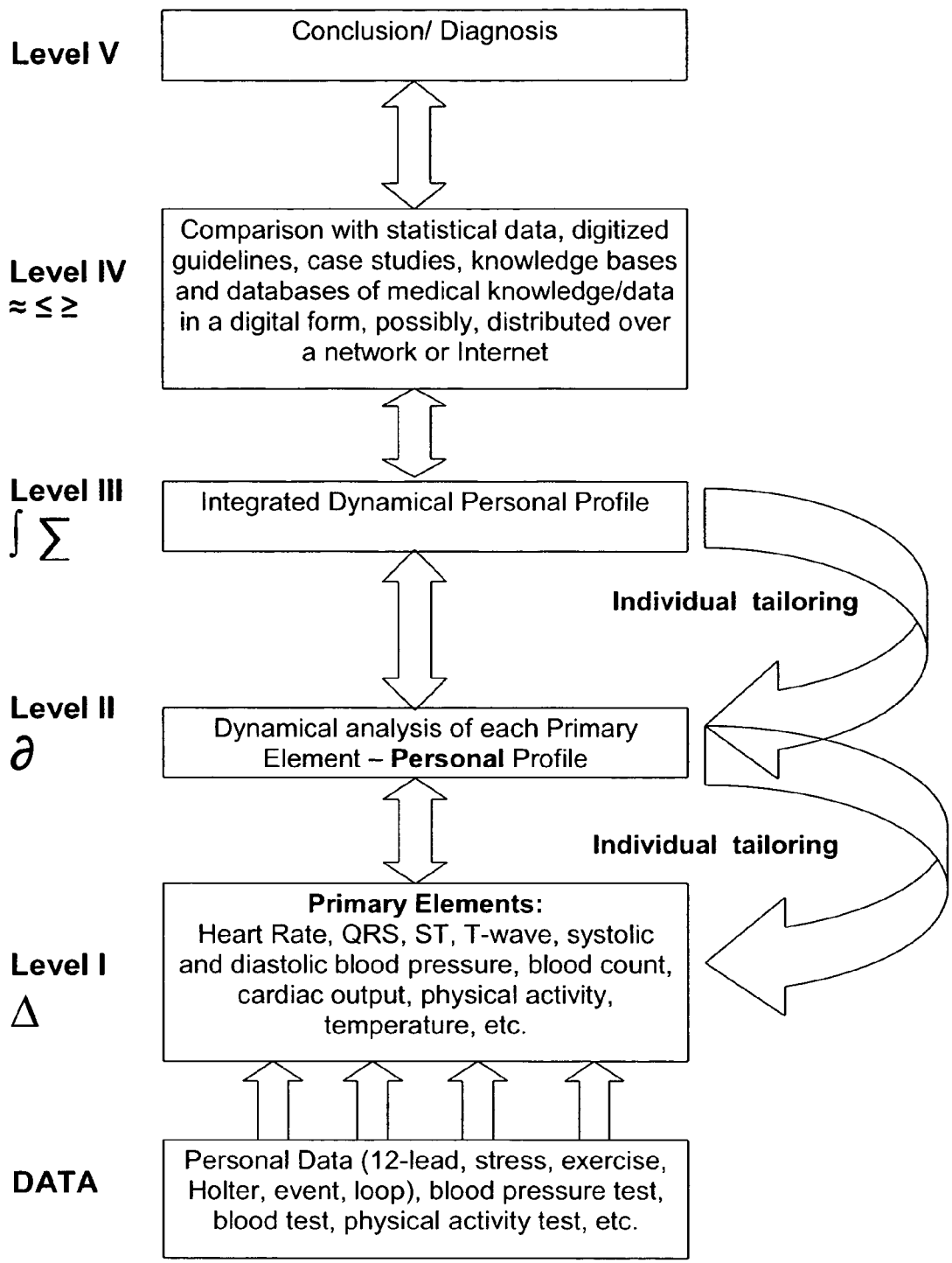
FIG. 15 is a flow chart of multi-scale analysis and representation of health data in accordance with this invention.
Figure 16:
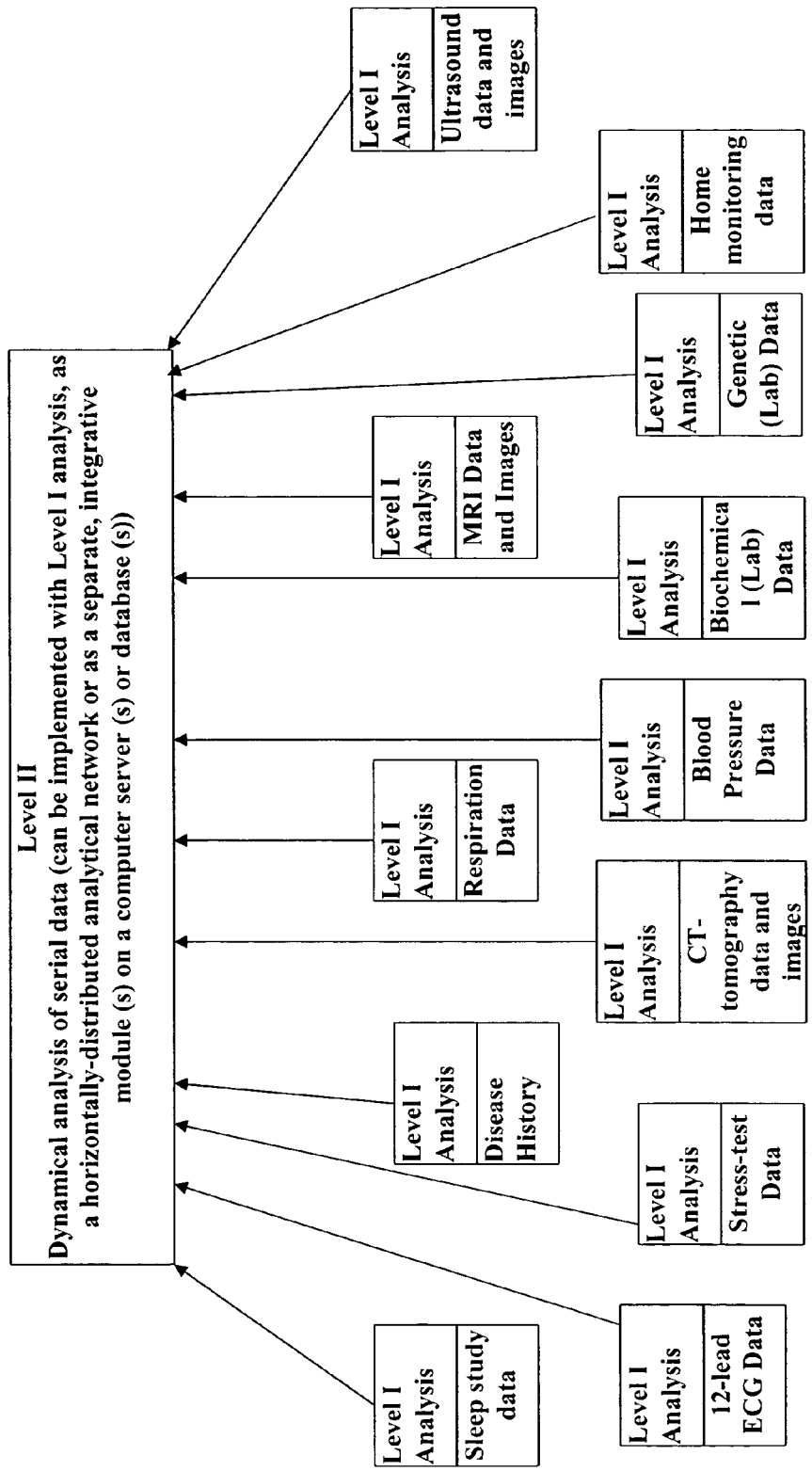
FIG. 16 is a flow chart showing horizontally and vertically distributed multiscale analysis and representation of health data in Levels I and II (with horizontally distributed Level I analysis).
Figure 17:
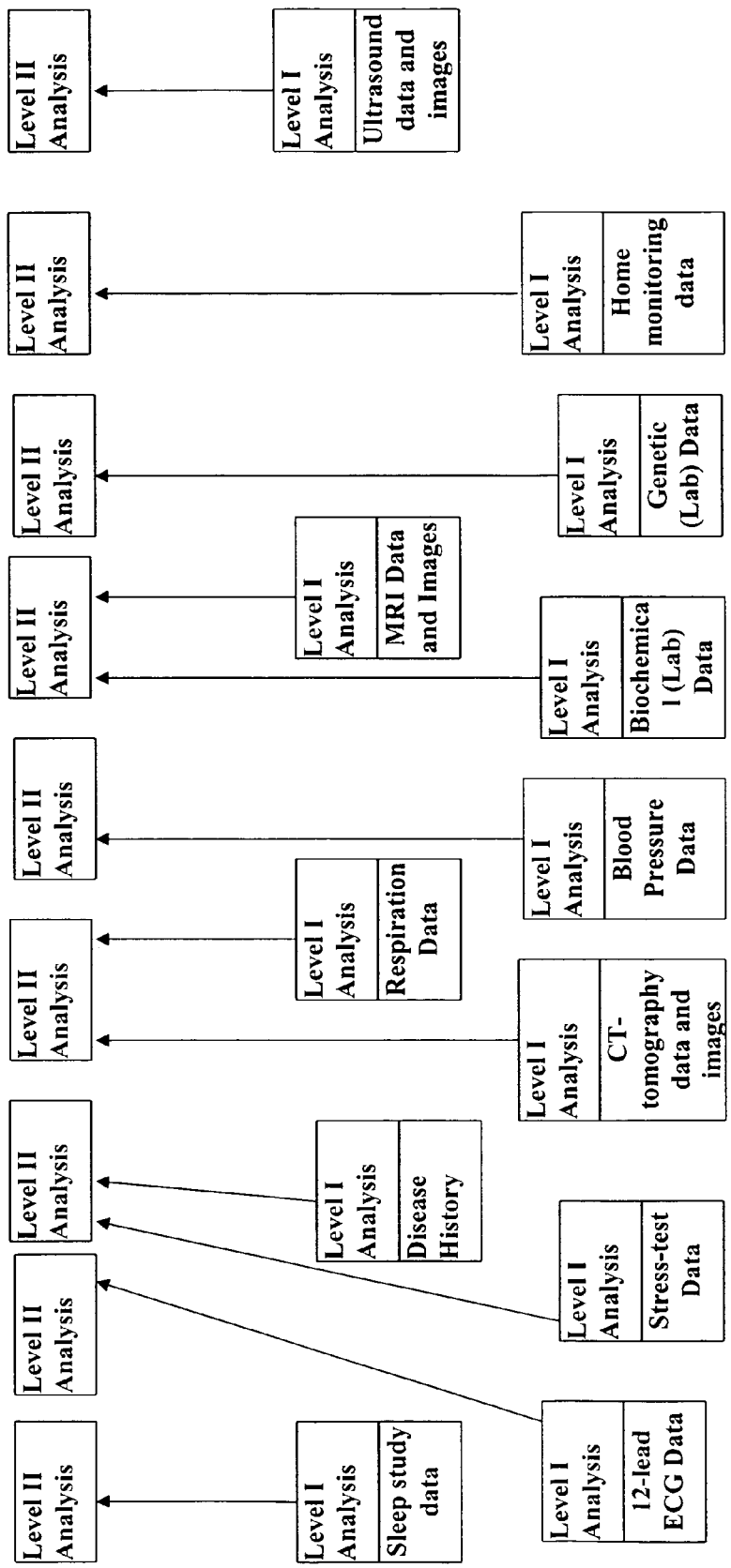
FIG. 17 is a flow chart showing horizontally and vertically distributed multiscale analysis and representation of health data in Levels I and II (with horizontally distributed Level I and II analyses).

Scale III. The same ECGs that were analyzed at the Scales I and II, were further processed by means of Scale III to expose the entire dynamics of the ECG signal. FIG. 13 demonstrates the ECG waveforms that were obtained from serial ECG recordings in patient A. Since all the data points are included into the analysis, the changes in the shape and polarity of T-wave can be easily detected in the serial ECGs using visual inspection, PCA or other signal processing tools. The polarity of the T-waves are negative in days 2 and 10 recordings, and are positive in days 6, 16 and 25 recordings.

Figure 14:
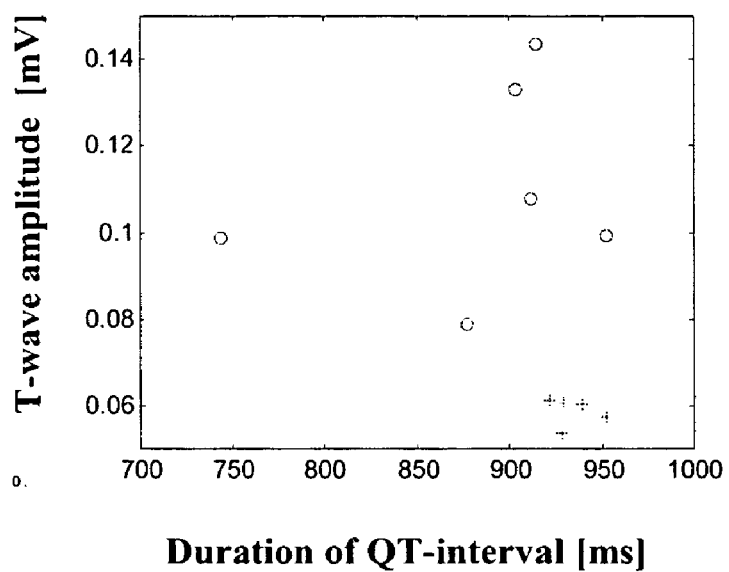
FIG. 14 is a plot of the first PCA-coefficient obtained from the series of QT-intervals versus the first PCA-coefficient obtained from the series of T-wave amplitudes in patient A.

FIG. 14 shows the changes in the PCA coefficients of these series in Scale III, dynamics of ECG in patient A in a space of the first, most significant PCA-coefficients. Y-axis represents the first PCA-coefficient that was obtained from T-wave amplitude. X-axis represents the first PCA-coefficient that was obtained from QT-interval. Each point corresponds to one-hour value. Values during 1-5 days are marked as pluses, values during 6-10 days are marked by stars, values during 11-16 days are marked by circles. Higher dispersion and change in the location of the points during 6-16 days compared to the first five days indicates instability of serial ECGs. A small cluster of data points in the lower right corner of the figure corresponds to the unchanged signals during the first 5 days of the recording. Then, the dispersion of the points increases and their location changes which reflects increased instability of the signals. Thus, the combined changes in the coefficients that were obtained from different primary elements revealed instability in the cardiac activity that preceded aggravation of the cardiac disease.

It is therefore seen that this invention provides an ECG analysis system and method for detecting a plurality of primary elements in an ECG signal, and comparing the detected signals with reference values both quantitatively and qualitatively. The outputs from the system in both low level resolution and higher levels of resolution can be understood by both lay persons and medical professionals. The system includes means for exchanging information and direction from an external computer for analysis and modification of the low resolution analysis of the signal.

The information exchange (including at least one of raw data such as electrocardiographic signals and results of analysis, such as primary elements derived from the electrocardiographic signal) from the lower scales to higher scales and back from the higher scales to the lower scales can be continuous or intermittent. For example, the $1^{st}$ lower-resolution scale can be implemented in a specialized, small-size sensor with a microprocessor, which continuously transmits data to the $2^{nd}$ scale, which can be implemented in a cell phone, a smart phone, a PDA, a computer, or a specialized processor. Thus, the $1^{st}$ scale sensor can transmit the data to the cell phone/PDA/smart phone/computer ($2^{nd}$ scale device) continuously or intermittently, when some changes in primary elements are identified. The $2^{nd}$ scale device can also transmit the data to the $3^{rd}$ scale, local or remote device (server) via a cell phone, Internet or other communication channels continuously or intermittently, when its analysis detects certain changes or when directed by a user. The data transmission between the $1^{st}$ and $2^{nd}$ scales and between the $2^{st}$ and the $3^{nd}$ scales can be done simultaneously or asynchronously.

Alternatively, the $1^{st}$ scale analysis can be implemented in a cell phone/PDA/smart phone/computer ($1^{st}$ level device), so that the sensor transmits the data to the $1^{st}$ level device continuously or intermittently (as programmed or directed by a user). The $1^{st}$ level device can also simultaneously display at least some of the received signals (in a real time or with a delay) and/or transmit them further to a remote or local $2^{nd}$ level device via a cell phone, internet or other communication channel continuously or intermittently, when certain changes are detected (for example, in some primary elements) compared to a baseline or pre-defined thresholds, or as directed by a user or by software settings (for example, once an hour).

Example II

The following example illustrates the sequence of ECG analysis at the system's Scales I, II and III. Serial ECG recordings from a patient A, who had a structural heart disease and dynamic changes in the electrocardiogram were processed at each Scale with a different degree of detail. Scale I revealed the changes in a small number of important, primary elements using minimum computational resources. Scale H exposed changes in the primary elements that occurred in serial recordings over time. Scale III provided complete description of the serial ECG changes using a complete set of primary elements and their combinations.

System initialization. When the system is used for the first time, initialization is required for verification and individual adjustment of the analysis criteria including identification of the primary elements and their search criteria. System initialization is performed using the hardware and software resources of the intermediate resolution Scale II and high resolution Scale III. In the initialization mode, the Scale I device transmits ECG to the higher Scale of the system via a direct or a wireless (telemetry or infrared) link. The ECG and the position of primary elements and their characteristic points (onset, peak, and offset) are visualized on a display, for example LCD display, as shown in FIG. 6. The position of characteristic points can be verified and manually edited by a user, a lay person or a medical professional. A simple manual or a software tutoring program of the typical ECG patterns, the primary elements and their characteristic points is provided for a lay person. FIG. 7 shows an ECG with a long QT-interval (0.5 sec) and a low-amplitude T-wave compared to the normal ECG shown in FIG. 6. The offset of this low-amplitude T-wave is difficult to detect automatically and a manual verification and correction are desired to ensure the accuracy. A user may also modify the set of monitored primary elements to account for a specific cardiovascular abnormality. Some of the elements may be combined into a single monitoring index, for example, a combined integral of T and U peaks can be useful for patients with possible electrolyte abnormalities.

After finishing manual verification and editing, the system automatically adjusts the search criteria for each characteristic point which include the time window, the amplitude, integral and derivative thresholds. The individually adjusted program is generated for a particular person and is automatically sent to re-program the processing sub-unit of Scale I. After the initialization, the Scale I device can work in autonomous regime without permanent connection to the higher-level Scales.

Re-initialization and serial adjustment can be performed to modify the set of primary elements and indexes and their search criteria. In addition to the procedure that was described in the system initialization, the results of the Scale II analysis can be used for serial adjustment. In particular, the primary elements and indexes whose time series and PCA coefficients demonstrate unstable behavior can be identified and included into the Scale I analysis.

Scale I. FIG. 7 is a graph of a representative electrocardiogram which has large Q-wave, and prolonged QT-interval. These abnormalities have been detected by the method of the present invention at the Scale I and represented qualitatively as abnormal findings and quantitatively as the exact magnitude of changes compared to the default values as shown in FIG. 8 which are readings of output indicators at Scale I for abnormal (A) and normal (N) ECG in the static mode. FIG. 9 is a graph of ECG obtained from the same patient several hours later. The amplitude of T-wave decreased by 0.3 mV compared to the previous recording shown in FIG. 8. The amplitude of T-wave decreased by 0.3 mV compared to the previous recording shown in FIG. 7. FIG. 9 shows the readings from the output indicators that represent the changes (C) in this ECG compared to the previous one.

Scale II. Serial ECGs have been obtained from patient A. and processed by means of Scale II to expose the time course of the serial changes that occurred in the this patient over a period of 1 month. FIG. 11, panel a, represents the series of QT-intervals that were extracted from these recordings; panels b-d demonstrate the changes in the first three PCA-coefficients that were obtained from this signal. At the end of the last recording, the patient developed a life-threatening disorder of cardiac function. However, this method reveals instability in the cardiac function as early as 20 days before the event when all known physiological indicators remain normal. FIG. 12 demonstrates changes in the T-wave amplitude extracted from the same recordings (panel a) and the corresponding first three PCA-coefficients. The time series are complex and the changes cannot be easily described or analyzed by simple tools, therefore, the changes in the signal are analyzed in a compressed form using the series of the first three PCA-coefficients which contain the most significant information about the signal. The ECG was relatively stable during the first 10 days but then became unstable as reflected by variations in the PCA-coefficients. The patient suffered a life-threatening cardiac disorder at the end of the month. However, variations in the PCA-coefficients were observed long before the event, when all physiological indicators remained normal. Calculating the changes in the variance of the PCA coefficients provides an accurate estimation of the changes and stability of the series. Unlike linear estimators such as the mean and variance of the signal or nonlinear estimators such as fractal scaling exponent or correlation dimension, disturbances in the PCA coefficients are indicative of any changes in the pattern of the signal. Therefore, analysis of PCA coefficients reveals both linear and nonlinear changes in the signal.

Scale III. The same ECGs that were analyzed at the Scales I and II, were further processed by means of Scale III to expose the entire dynamics of the ECG signal. FIG. 13 demonstrates the ECG waveforms that were obtained from serial ECG recordings in patient A. Since all the data points are included into the analysis, the changes in the shape and polarity of T-wave can be easily detected in the serial ECGs using visual inspection, PCA or other signal processing tools. The polarity of the T-waves are negative in days 2 and 10 recordings, and are positive in days 6, 16 and 25 recordings.

FIG. 14 shows the changes in the PCA coefficients of these series in Scale III, dynamics of ECG in patient A in a space of the first, most significant PCA-coefficients. Y-axis represents the first PCA-coefficient that was obtained from T-wave amplitude. X-axis represents the first PCA-coefficient that was obtained from QT-interval. Each point corresponds to one-hour value. Values during 1-5 days are marked as pluses, values during 6-10 days are marked by stars, values during 11-16 days are marked by circles. Higher dispersion and change in the location of the points during 6-16 days compared to the first five days indicates instability of serial ECGs. A small cluster of data points in the lower right corner of the figure corresponds to the unchanged signals during the first 5 days of the recording. Then, the dispersion of the points increases and their location changes which reflects increased instability of the signals. Thus, the combined changes in the coefficients that were obtained from different primary elements revealed instability in the cardiac activity that preceded aggravation of the cardiac disease.

Example III

This theoretical example has been selected to show how the present invention could be implemented using a distributed network of computers with parallel processing and how it can be efficiently integrated with such methods of artificial intelligence as neural networks and expert systems to process different types of serial information obtained from a patient with chronic congestive heart failure. Patients with chronic illnesses often have a number of chronically or intermittently abnormal indicators, whose dynamics are difficult to discern. A network of computers allows fast and accurate processing of the patient's information obtained using different diagnostic techniques (such as biochemical, electrocardiographic, nuclear magnetic resonance, stress-test, and other modalities).

In a hypothetical patient B. with chronic congestive heart failure (Class II) and a three-year-old myocardial infarction, the above-described high-resolution analysis of serial ECG recordings could reveal a subtle decreasing trend in the amplitude of the ST-segment. This trend could be revealed because the serial ECG recordings were processed at the high-resolution level using a radial basis function (RBF) neural network, which was previously trained on patient's B. electrocardiographic data. Because the neural network could learn the typical patient's B. ECG pattern, it could detect subtle changes in this pattern. The magnitude of the changes may be so small and the changes so gradual, that they might escape detection by the standard ECG processing techniques, which are manually applied by the physicians or used by the current commercial ECG scanning software. The computer server, where ECG recordings from this and other patients would be stored and analyzed, would be a part of a computer network that also includes servers for analysis of biochemical, stress-test, nuclear magnetic resonance, and other data. The servers would be organized into a hybrid artificial intelligence system, which combines a neural network and expert systems. In this system, the neural networks are used where the rules of analysis can be modeled by a multi-node network structure, in which each node is assigned the specific input and output rules and connections to other nodes. On the other hand, expert systems are used when the decision making process due to numerous uncertainties is better represented by informal (heuristic) rules.

The above-described decreasing ST-amplitude trend in the serial ECG recordings lead to an activation of an expert system's rule that initiates query of other computer servers on the network that contain biochemical, stress-test, and nuclear-magnetic resonance date for the same patient. After that, the server that contained biochemical data initiates neural network analysis of the patient's enzyme level concentration for the period of time, in which ECG changes occurred. A small increasing trend is detected in the cardiac myoglobin levels, and this biochemical and ECG information are transmitted wirelessly to the personal digital assistant of an attending physician with a suggestion of a slowly developing ischemic process. The timely notification allows the physician to initiate early anti-ischemic treatment and prevent potentially life-threatening complications of the disease.

Example IV

This theoretical example is provided to show implementation of the present invention on a specialized computer network, which could be setup for individuals working in the high-demand professional environments, such as airplane pilots.

During a late-spring commercial flight, a hypothetical 46-year-old pilot suddenly developed dizziness and shortness of breath. A Scale I ECG examination showed sinus tachycardia (fast heart rates) and increased amplitude of the P-wave. The Scale I analysis is performed using a portable ECG acquisition unit, which transmitted the information wirelessly (using a Bluetooth radiofrequency communication technology to an integrated airplane health network (implemented using Wi-Fi wireless technology). A second Scale-I-device (also connected to the network) is used to examine changes in blood pressure and detected moderate increase in diastolic pressure.

The airplane integrated health system, which includes a diagnostic expert system, queries wirelessly the home network computer server of the pilot (using GPS wireless communication technology) to obtain the health data for the previous month. The home network server, in turn, activates Scale II serial analysis of all available health data and detects subtle but gradually increasing instabilities in heart rate and P-wave amplitude during the previous 3 days aggravated by physical exercises. In the health data file, the system also identifies information regarding the pilot's history of allergic reactions during the spring vegetation periods. This information is transmitted back to the airplane expert system, which combines the information and suggested an allergic bronchial spasm. This information is transmitted wirelessly to the personal digital assistant of an attending physician, who from his home network system sends back a recommendation of anti-allergic medication, which eliminates the symptoms.

Note that the multi-scale distributed system could be configured to operate in several different modes. In the first mode, which is activated in the airplane, the portable ECG acquisition and Scale-I-analysis unit transmits the data wirelessly to the integrated airplane health network for higher-resolution analysis. In the second mode, which is activated in a car, the portable Scale-I-analysis unit communicates wirelessly with the car computer network using a bluetooth technology. In the third mode (which is activated at home), the portable ECG acquisition and Scale-I-analysis unit transmits the data wirelessly to the home integrated computer health network (organized using Wi-Fi communication). In the fourth configuration (which is usually activated outside home, on vacations, etc.), the portable ECG acquisition and Scale-I-analysis unit transmits the data wirelessly to the personal digital assistant (PDA) or a cell phone or a smart phone (a combination of a cell phone and a PDA) for Scale II analysis. If needed, this Scale-II-analysis unit then connects wirelessly (using a cell phone GSM communication technology) to a home health computer network. Alternatively, this fourth mode of operation (with a PDA or a cell phone for Scale II analysis) could be selected to operate at home, in a car, in the airplane, and in other settings.

Example V

This theoretical example is selected to show application of the present invention for tracking dynamics of health data in patients with implantable cardiac devices.

A hypothetical patient with an implantable cardioverter-defibrillat- or has developed subtle instabilities of cardiac rhythm and slowly rising average heart rate. These changes are detected by the implantable device, which transmits this information wirelessly to a home health network computer. The network computer performs serial analysis of the recordings at Scale III resolution. At the same time, the computer reaches a hospital network server and queries the recordings from the same patient during his recent hospitalization. Inclusion of these recordings into the Scale III analysis shows that a similar instability of heart rate was observed in this patient only prior to onset of life-threatening cardiac arrhythmia. Another personal device (also connected to the network) for tracking changes in blood pressure shows instability of blood pressure. An artificial intelligence system (which was integrated with the Scale III analysis) is automatically activated to interpret these findings. The system assesses the findings as clinically significant and forwards them wirelessly to a personal digital assistant of an attending physician, who decides to initiate preventive beta-blocking therapy. During the next six hours of monitoring, the Scale II and Scale III analysis shows stabilization of cardiac rhythm.

Example VI

This theoretical example describes potential benefits of the present invention in patients with congestive heart failure undergoing bi-ventricular resynchronization pacing therapy (using the implanted bi-ventricular pacing device, such as a Medtronic Insync Marquis III™ device or a Medtronic Optivol).

A hypothetical patient with chronic congestive heart failure undergoing resynchronization pacing for 15 months has developed a gradual increase in the intrathoracic impedance, detected by Optivol, indicative of slowly progressing decompensation of cardiac function. These changes are detected by the implanted device, which used individually tailored monitoring thresholds at the Scale I analysis. The thresholds were adjusted using the individual patient's reference values determined at the Scale II-II analysis (which was performed on a hospital health network). The changes in the intrathoracic impedance detected by the implanted device with Optivol are transmitted wirelessly to the hospital computer network for higher-resolution, in-depth processing. The Scale II-III analysis confirms that the magnitude of the changes exceeded 3 standard deviations never been observed in this patient previously. The information is transferred to the integrated artificial intelligence system for further interpretation. The system classifies the changes as clinically significant and forwarded them to the medical personnel. Considering these changes, a decision is made to hospitalize the patient for detailed examination and therapy adjustment.

A similar hypothetical example can be envisioned for a patient with an implantable device having several sensors, such as the intrathoracic impedance sensor and the intra-atrial pressure sensor. The analyses at the $1^{st}$ and $2^{nd}$ scales for each sensor's data would be performed as described above. However, at scale III analysis, the data obtained from both sensors will be integrated to obtain an integrated, personalized, dynamical profile. If the trends of data obtained from both sensors are consistent with progressive deterioration of cardiac function, this would increase the probability of a dynamical diagnosis of a heart failure worsening. However, if the trends of data obtained by both sensors are contradictory, the probability of a diagnosis would decrease.

A hidden Markov model (HMM) could be used to track the dynamic probability of a change in the state of a disease (for example, heart failure worsening). For example, a left-right HMM can be constructed in such a way that the probability of a change in the disease (heart failure) state is associate with a set of parameters $\Theta=\{\pi, A, B\}$, where $\pi$ is a prior probability (i.e. the probability that the subject is initially at a certain state of heart failure), A is a transition matrix of probabilities of going from one state of the disease (heart failure) to another, and B is a matrix of emission probabilities that describe the likelihood of a certain symptom or a diagnostic indicator (primary element) or a change (dynamics) in the properties of the primary elements when the subject's disease (heart failure) is in a certain state (for example, the heart failure NY state III). If the symptoms (or primary elements) are continuous, then the matrix B contains functions, probability density functions, vectors, or mixtures of functions. The above matrices can also contain some parameterizations derived from the data, such as mean/median values and variances or ranges.

The joint likelihood of a sequence of serial changes in data or its primary elements (i.e. the likelihood that an observed sequence of dynamic changes in data or primary elements occurs when a certain sequence or path of changes in the disease (heart failure) status, Q, occurs) can be computed using Bayes conditional probability:

$$P(X,Q|\Theta)=P(X|Q,\Theta) \cdot P(Q|\Theta) \quad (6)$$

$$\text{where } P(X|Q, \Theta) = \prod_{n=1}^{N} P(x_n|q_n, \Theta) = b_{q_1,x_1} \cdot b_{q_2,x_2} \cdots b_{q_N,x_N} \quad (7)$$

Formula (7) represents the likelihood of a certain sequence of changes in primary elements, X, along a certain path of changes in the disease (heart failure) states, Q. Next, probability of a sequence of disease (heart failure) states given a set of parameters $\Theta$ is equal to a product of transition probabilities along this path.

$$P(Q|\Theta) = \pi_{q_1} \cdot \prod_{n=1}^{N-1} a_{q_n, q_{n+1}} = \pi_{q_1} \cdot a_{q_1, q_1} \cdot a_{q_2, q_3} \cdots \cdot a_{q_{N-1}, q_N} \quad (8)$$

Using formulas (6)-(8), one can compute the likelihood of an observed sequence of dynamic changes in data or primary elements for each sequence or path of changes in the disease (heart failure) state, Q. Then, one can determine the sequence or path of changes in the disease (heart failure) state associated with the greatest likelihood, and this will be the most likely sequence of changes in the disease state. To reduce the amount of computations, this analysis can be implemented in software using a recursive Viterbi algorithm, or other recursive, forward-backward computer algorithms. To represent (visualize) the dynamic changes in the probabilities of different diseases (or disease states) for a user, one can use Trellis diagrams.

To determine the most probable HMM for a given sequence of serial changes in the primary elements or data, one can compute first, for each HMM, the probability of the most likely path (sequence) of changes in the disease state as described above (see (6)-(8)). Then, an HMM that has the greatest probability of the most likely path would be the most probable HMM model.

One can also compute a normalized probability of an HMM, by normalizing the probability of the most likely path (sequence) of changes in the disease state for each HMM, by a sum of the joint likelihoods for the particular sequence of serial changes in primary elements and all possible disease (heart failure) states, Q, allowed by the HMM as follows:

$$P(X|\Theta) = \sum_{allQ} P(X, Q|\Theta) \quad (9)$$

Equation (9) also provides a way to compute the probability of observing a certain sequence of serial changes in the primary elements or data for a given HMM (over all disease states). Using formula (9) for different HMMs, allows one to determine a model (among several models), which gives the greatest probability of observing a particular sequence of serial changes in the primary elements or data.

It is also possible to construct a second-order Markov model in which the probability of a certain disease (heart failure) state will depend on 2 previous states (unlike in the $1^{st}$ order Markov model, where the probability of a state depends only on the previous state). Obviously, the idea of the order of the model can be generalized to any other number n=3, 4, 5 ... N.

It is also possible to "train" HMM on data with known properties to determine the optimal set of parameters ($\Theta=\{\pi, A, B\}$ defined above) that maximize the accuracy of the model with respect to determination of a disease state or serial changes in disease state (disease state sequence). The "training" goal could be determined according to the specifics of a particular healthcare application.

Note that the description of applications of the hidden Markov models for analysis of the disease/health dynamics is not limited to patients with implantable devices or patients with heart failure. The Markov models and hidden Markov models, as well as other Bayesian, probabilistic models/networks, can be used for dynamic analysis of any disease state or health data in any population or individual. These analytical tools can be also used for tracking the probabilities of presence/changes in several possible diseases (differential diagnosis).

Example VII

This theoretical example describes one of the applications of the multi-scale monitoring system in a hospital setting for information management, diagnosis, and decision support. A hypothetical patient has been hospitalized with chest pain and an electrocardiographic ST-depression with a tentative diagnosis of unstable angina. His vital signs remained within physiologically normal limits. The information from his ECG monitoring system, blood pressure, blood count, biochemical examination, cardiac echocardiography, heart computer tomography, and other tests has been transmitted into the system from the respective systems and services (FIG. 1, bottom scale). The analysis at Level I has confirmed presence of ST-depression in the electrocardiogram. The analysis is Level II, by comparing the present ECG with previous ECGs collected from the same patient during previous hospital visits has showed that the ST-depression has become much more pronounced, suggesting developing of acute or unstable angina. In addition, the system identified a subtle, gradual, but significant trend towards increase in the QT-interval, which might indicate a heightened risk of a cardiac arrhythmia. The abnormal trend in QT-intervals has been highlighted as abnormal and potentially dangerous using color-coding (red color) to draw attention of medical personnel. Analysis at Level III also showed that a combination of a chest pain, which has gradually intensified during the last 24 hours and the ST-depression has never occurred before in this patient, also confirmed presence of an acute coronary syndrome. At Level IV, the system has used statistical data, pattern recognition, and artificial intelligence to compare the patient's data with general information about different diseases (from a medical knowledge base available in a digital form on the network) that can cause chest pain and ST-depression and determined the list of possible diseases and stages of the diseases, with their respective probabilities. This analysis confirmed that acute, unstable angina was the most probable cause of the patient's current problem. As a result of the system's analysis, the diagnosis has been confirmed within a very short time, which resulted in an appropriate treatment initiated in a timely fashion and helped avert potential complications, such as myocardial infarction and arrhythmias.

Example VIII

This theoretical example describes one of the applications of the multi-scale monitoring system in an out-hospital (ambulatory) setting for information management, diagnosis, and decision support. A hypothetical patient at home experienced a chest pain. Using a personalized ECG system, the subject recorded his ECG and sent it using a wireless (cell phone) transmission to a remote computer center, where the patient's historic data has been stored. This information along with the subject's complaint on the chest paint has been entered in the information management system (FIG. 1, bottom). The system has processed the ECG (Level I) and identified that all primary elements (amplitudes and durations of all ECG complexes) are within normal range. At the next Level II, the most current values of primary elements (amplitudes and durations of P, Q, R, S, T-waves, QT-interval, QRS-complex, ST-interval, T-wave alternans) were compared with historic data obtained from the same subjects during previous ECG examinations. The system did not identify any trends or changes in the data using the comparative analysis of serial data. Thus, the results of serial ECG analysis were highlighted with a green color, which indicates a normal range and trend. At the Level III, the system combined the patient's complains on chest pain with the ECG-findings and compared with previous (historic) findings of chest pain and ECG-patterns obtained from the same patient over a 3-year period. No changes were identified with respect to previously recorded perception of chest pain or the ECG-pattern. At the next Level IV, the system compared the findings with the previously identified in this patient finding of degenerative disk pathology in the thoracic part of the spine and with the general medical knowledge base containing symptoms of different diseases. This comparative analysis has determined that the most probable cause of the patient's symptoms is related to the degenerative disk disease. This information has been transmitted to the physician's smart phone from the information management system wirelessly, and the physician referred the patient to an orthopedic surgeon. Thus, the information management system helped to avoid unnecessary emergency visit into the Emergency Room and unnecessary diagnostic tests and examinations, streamlined and reduced the time and cost of the diagnosis.

In addition to the above-described orthogonal linear decomposition, other methods of non-orthogonal decomposition or independent component analysis, multidimensional scaling based on non-metric distances and mapping techniques can be used for multi-scale analysis. These include but are not limited to non-orthogonal linear mappings, nonlinear mappings and other projection methods that make use of such mathematical tools as the domain and range straightening, and re-scaling (change of variables), methods from the theories of singularities, bifurcations, catastrophes, and dynamical systems. In addition, other statistical estimators, such as a linear and nonlinear correlation, analysis of variance, cluster analysis, factor analysis, canonical analysis, regression and discriminant function analysis, and probabilistic methods, such as Bayesian probability, pattern recognition, and methods of artificial intelligence, including neural networks, fuzzy logic, and expert systems, as well as hybrid (combined) artificial intelligence systems, can be applied for estimating the temporal changes in the physiological data and in the derived variables at different scales (resolutions).

Further implementation of the multi-scale analysis is possible to provide detailed characterization of serial changes using a fuzzy logic classifier or a dynamic neural network with at least one neuron (unit) analyzing changes in one or more states of activity of at least one physiological, biochemical, biophysical, mechanical, or genetic system relative to at least one reference value. For example, such a system could be used to examine changes in activities of the sympathetic and parasympathetic nervous systems over short or long periods of time during sleep, physical, or psychological tests. As another example, the above-described system could be used to characterize dynamics of a chronic disease, such as congestive heart failure, first, by analyzing changes in each physiological indicator (such as heart rate, blood pressure, or cardiac output) at rest and during various physical activities in comparison with individual reference values (Scale I, II), and second, by combining the results of Scale-I-and-II-analyses into a general assessment of changes in the patient's condition (Scale III). Furthermore, the reference values could be represented either by a single parameter or by a relation (mathematical function or statistical distribution) between said reference values and a state or states of physiological, biochemical, biophysical, mechanical, or genetic system. For instance, a reference value could represent a range of changes in a physiological parameter, such as heart rate, over 24 hours or during a stress test. Although these methods are substantially different from each other, a novel, unifying feature of the present invention is that the information is processed at different scales (levels of resolution or details) and that the different levels of processing can be distributed among computers and devices on a network. Thus, in a framework of the present invention, each of the above-described methods could be implemented instead of the linear orthogonal decomposition for multi-scale distributed analysis of physiological data, exchange of the results between the scales, and representation of the results of multi-scale analysis for lay people and medical professionals. In particular, an artificial intelligence system (an expert system or a neural network) can be implemented using a multi-layer structure, in which each layer of processing rules or nodes (elementary units on the neural net or objects in the expert system) has a different processing resolution (scale). Thus, this structure can have a low-resolution processing (Scale I) and a higher-resolution processing scheme (Scales II and III), as described by the present invention. Such artificial intelligence systems could be used for the types of physiological data that could be modeled by interconnected nodes with elementary input and output operations (a neural network) or could be represented by informal (heuristic) rules of processing (an expert system), or could be implemented in a combined system of rules and nodes (a hybrid system). Although these methods are very general and widely used in different applications, the present invention describes a novel multi-resolution (multi-scale) structure of these systems and its applications for dynamic analysis of subtle changes in health data.

As another example, Mahalanobis distance, a measure of distance between two points in the space defined by two or more, possibly, correlated variables can be used to determine the probability of a change in the physiological data at different scales. For each variable, the location of the point mean steady-state value (centroid 1) and the mean unsteady value (centroid 2) are determined. Mahalanobis distances from the steady-state and the unsteady centroids to each data point are then calculated. The probability that a point belongs to the steady-state or the unsteady sector is proportional to the Mahalanobis distance from that sector centroid. These distances, for example, could be used for the estimation of temporal changes in electrocardiographic T-wave amplitude shown in FIG. 13. In particular, the probability of a change in the new T-wave amplitude data at a low-resolution scale can be determined using Mahalanobis distance between the new data and the two centroids (steady-state and unsteady one). At the higher-resolution scale, the probability of a change, its magnitude, and other characteristics could be estimated more precisely by separating the steady-state and the unsteady sectors into sub-sectors, determining the corresponding centroids, and estimating Mahalanobis distances between the new data and the centroid of each sub-sector. The locations of the centroids are updated after the new data are collected to provide time-adjusted, individual reference or baseline values. The distances between the centroids demonstrate the individual range of variations in the studied variables, which can be compared to the average values in a group or a population. Mahalanobis distances can also be used to estimate the changes in combinations of variables.

This procedure is similar to the inclusion of additional dimensions (components) into the PCA. However, unlike PCA, the nonlinear estimation or an artificial intelligence approach is not limited to orthogonal components and metric distances, but may include non-orthogonal components (also referred to as the independent components) and nonlinear estimators.

It is therefore seen that this invention provides a physiological data analysis system and method for detecting a plurality of primary elements and comparing the detected elements with reference or baseline values both quantitatively and qualitatively. The outputs from the system in both low level resolution and higher levels of resolution can be understood by both lay persons and medical professionals. The system includes means for exchanging information and direction from an external computer for analysis and modification of the low resolution analysis of the signal. The system further includes mathematical methods and applications described in Shusterman's U.S. Pat. Nos. 6,389,308 and 6,925,324, which are incorporated herein by reference.

Whereas particular aspects of the method of the present invention and particular embodiments of the invention have been described for purposes of illustration, it will be appreciated by those skilled in the art that numerous variations of the details may be made without departing from the invention as described in the appended claims.

What is claimed is:

1. A method useful in healthcare information management comprising:
    collecting at least one primary element as a snapshot present at the time of recording of health data using at least one collection method selected from one-time, periodic, quasi-periodic and continuous monitoring, and electronically comparing said at least one primary element with at least one reference value to detect changes in said at least one primary element and thereby identify any abnormal or unstable primary element (a first-level, low-resolution analysis); and
    analyzing serial changes in said at least one primary element of health data using a dynamic serial analysis and processing unit employing at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Markov model, hidden Markov model, and Mahalanobis distance, pattern recognition, fuzzy logic, neural networks, expert systems, and hybrid artificial intelligence systems to provide detailed characterization of serial changes in any abnormal or unstable primary element (a second-level, higher resolution serial analysis).

2. A method as set forth in claim 1 which includes distribution to at least one computing device having access to medical knowledge on the Internet to incorporate said medical knowledge into said serial analysis.

3. A method as set forth in claim 1 which includes distribution to at least one computing device having access to digitized medical journals, books and other publications to incorporate information from such journals, books and publications into said serial analysis.

4. A method as set forth in claim 1 in which said collecting at least one primary element and electronically comparing said at least one primary element with at least one reference value to detect changes in said at least one primary element and thereby identify any abnormal or unstable primary element (a first-level, low-resolution analysis) of health data is performed repeatedly over time.

5. A method as set forth in claim 4 in which said healthcare information is collected and analyzed substantially continuously for a period in a range of at least several minutes to many days.

6. A method as set forth in claim 1 that includes personalized adaptation of diagnostic criteria.

7. A method as set forth in claim 1 which includes analyzing at least one primary element in said data as a snapshot present at the time of recording of health data and comparing said at least one primary element with at least one reference value in a first-level, low resolution using at least one method selected from mathematical decomposition, mathematical modeling, computer modeling, time-series analysis, pattern recognition, signal processing, probabilistic methods, statistical analysis, and methods of artificial intelligence to detect changes in said at least one primary element and thereby identify any abnormal or unstable primary element (low-resolution analysis).

8. A method as set forth in claim 1 in which said first-level analysis and said second-level analysis exchange information using a wireless communication device selected from at least one of a cell phone, smart phone, PDA, Wi-Fi, and other types of radio-transmitters and communication devices.

9. A method as set forth in claim 1 in which analyzing said data to provide detailed characterization of serial changes in said abnormal or unstable primary elements is selected from a fuzzy-logic classifier and a dynamic neural network with at least one neuron (unit) analyzing changes in at least one state of activity of at least one physiological, biochemical, biophysical, mechanical, and genetic system relative to at least one reference value.

10. A method as set forth in claim 7 in which said at least one reference value is represented by a relation (function, distribution) between said reference value and at least one state of at least one physiological, biochemical, biophysical, mechanical, and genetic system.

11. A method as set forth in claim 1, in which said analyzing serial changes is applied to physiological signals selected from at least one of electrocardiogram, electroencephalogram, magnetocardiogram, pulse oximetry, impedance, magnetic resonance (MRI), computed tomography (CT), ultrasound, fluoroscopic, X-ray imaging, stress-test, physical activity, clinical symptoms, chest pain, shortness of breath, nausea, blood pressure, cardiac output, vascular activity, temperature, respiration, cardiac, abdominal, or breathing sounds, blood flow, hormonal concentration, physical activity, blood tests, weight, heart rate, enzyme and protein level, genetic, genomic, proteomic, metabolomic, and molecular data, neural activity, electroencephalographic activity, and other electrical, mechanic, sonic, biochemical, biophysical processes in the human body, demographic, psychological, and environmental data.

12. A method as set forth in claim 1 in which at least one of information completeness and a probability of a certain disease is tracked dynamically in at least one level of analysis.

13. A method as set forth in claim 1 in which at least one of information completeness and a probability of a certain disease is tracked dynamically in at least one database.

14. A method useful in healthcare information management comprising:
- analyzing at least one primary element of health data by electronically comparing a snapshot of data recorded respecting said at least one primary element with at least one reference value to detect changes in such primary element and thereby identify any abnormal or unstable primary element (a first-level, low resolution analysis);
- analyzing serial changes in said at least one primary element using a dynamic serial analysis and processing unit employing at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scalin (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Markov model, hidden Markov model, and Mahalanobis distance, pattern recognition, fuzzy logic, neural networks, expert systems, and hybrid artificial intelligence systems to provide detailed characterization of any serial changes in abnormal or unstable primary element (a second-level, higher resolution analysis); and
- analyzing changes in said at least one primary elements in a third level resolution, using at least one dynamic analysis and processing unit, which includes combining the analysis of primary elements with digitized personal health data.

15. A method as set forth in claim 14 which includes distributing data produced by said second level analysis to at least one computing device having access to medical knowledge on the Internet to incorporate such knowledge into said second level analysis.

16. A method as set forth in claim 15 in which said distribution includes at least one computing device having access to digitized medical journals, books and other publications to incorporate medical knowledge from said publications into said second level analysis.

17. A method as set forth in claim 14 in which said collecting at least one primary element and electronically comparing said at least one primary element with at least one reference value to detect changes in said at least one primary element and thereby identify any abnormal or unstable primary element (a first-level, low-resolution analysis) of health data is performed repeatedly, seriatim over a prolonged period.

18. A method as set forth in claim 14 in which health data are analyzed substantially continuously for a period in a range of at least several minutes to many days.

19. A method as set forth in claim 14 in which said analyzing a plurality of primary elements in said data in first-level low resolution is selected from at least one of mathematical decomposition, mathematical modeling, computer modeling, time-series analysis, pattern recognition, signal processing, probabilistic methods, statistical analysis, and methods of artificial intelligence.

20. A method as set forth in claim 14 in which analyzing said data to provide detailed characterization of serial changes in said abnormal or unstable primary elements is performed using at least one wireless communication device selected from at least one of a cell home, smart phone, PDA, Wi-Fi, and other types of radio-transmitters and communication devices.

21. A method as set forth in claim 14 in which analyzing said data to provide detailed characterization of serial changes in said abnormal or unstable primary elements is selected from a fuzzy-logic classifier and a dynamic neural network with at least one neuron (unit) analyzing changes in at least one state of activity of at least one physiological, biochemical, biophysical, mechanical, and genetic system relative to at least one reference value.

22. A method as set forth in claim 14 in which said reference values are represented by a relation (function, distribution) between said reference values and at least one state of at least one physiological, biochemical, biophysical, mechanical, and genetic system.

23. A method as set forth in claim 14 in which at least one of said first, second and third level analysis is applied to physiological signals selected from at least one of electrocardiogram, electroencephalogram, magnetocardiogram, pulse oximetry, impedance, magnetic resonance (MRI), computed tomography (CT), ultrasound, fluoroscopic, X-ray imaging, stress-test, physical activity, clinical symptoms, chest pain, shortness of breath, nausea, blood pressure, cardiac output, vascular activity, temperature, respiration, cardiac, abdominal, or breathing sounds, blood flow, hormonal concentration, physical activity, blood tests, weight, heart rate, enzyme and protein level, genetic, proteomic, and molecular data, neural activity, electroencephalographic activity, and other electrical, mechanic, sonic, biochemical, biophysical processes in the human body, demographic, psychological, and environmental data.

24. A method as set forth in claim 14 in which at least one of information completeness and a probability of a certain disease is tracked dynamically in at least one level of analysis.

25. A system useful in healthcare information management comprising:
- a first analysis and processing unit for analyzing a snapshot of at least one of a plurality of primary elements from recorded health data and processing said at least one primary element to generate data respecting said at least one primary element, and comparing at least one reference value respecting said at least one primary element with data newly received by said first analysis and processing unit and producing at least one indicator respecting any differences between said at least one reference value and said newly received data (a low resolution analysis),
- a second analysis and processing unit for processing health data collected over time using at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), mathematical modeling, computer modeling, signal processing, time-series analysis, statistical analysis, multidimensional scaling based on non-metric distances and mapping techniques, non-orthogonal linear mappings, nonlinear mappings and other methods that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Markov model, hidden Markov model, and Mahalanobis distance, pattern recognition, fuzzy logic, neural networks, expert systems, and hybrid artificial intelligence systems to detect serial changes in said at least one primary element (higher resolution analysis); and a communications unit for exchanging information between said first and second analysis and processing units.

26. A system as set forth in claim 25 which includes at least one acquisition unit for collecting data using at least one collection method selected from one-time, periodic, quasi-periodic and continuous monitoring.

27. A system as set forth in claim 25 in which said communications unit is adapted to distribute data to at least one computing device having access to medical knowledge on the Internet to incorporate said medical knowledge into said higher resolution analysis.

28. A system as set forth in claim 25 which includes a third level of resolution that comprises personalized adaptation of diagnostic criteria.

29. A system as set forth in claim 25 in which said first analysis and processing unit and said at least one computer device for analyzing a snapshot of at least one of a plurality of primary elements use at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Markov model, hidden Markov model, and Mahalanobis distance, pattern recognition, fuzzy logic, neural networks, expert systems, and hybrid artificial intelligence systems.

30. A system as set forth in claim 25 in which at least one of said first analysis and processing unit and said at least one computer device analyze physiological data selected from at least one of electrocardiogram, electroencephalogram, magnetocardiogram, pulse oximetry, impedance, magnetic resonance (MRI), computed tomography (CT), ultrasound, fluoroscopic, X-ray imaging, stress-test, physical activity, clinical symptoms, chest pain, shortness of breath, nausea, blood pressure, cardiac output, vascular activity, temperature, respiration, cardiac, abdominal, or breathing sounds, blood flow, hormonal concentration, physical activity, blood tests, weight, heart rate, enzyme and protein level, genetic, proteomic, and molecular data, neural activity, electroencephalographic activity, and other electrical, mechanic, sonic, biochemical, biophysical processes in the human body, demographic, psychological, and environmental data.

31. A system as set forth in claim 25 in which said communication unit is wireless.

32. A system as set forth in claim 25 in which said second analysis and processing unit is connected to several computers via a computer network for at least one of visualization and analysis of the health data.

33. A system as set forth in claim 25 in which said first analysis and processing unit is connected to several personal devices selected from noninvasive and implantable devices for data acquisition and low-level analysis of health data.

34. A system as set forth in claim 25 in which said higher resolution analysis of health data is performed using parallel processing.

35. A system as set forth in claim 25 in which said higher resolution analysis of health data is distributed among several computers connected via specialized computer networks, selected from networks for home use, work environment, hospital, and transportation.

36. A system as set forth in claim 25 in which said higher resolution analysis of health data is distributed among several computers connected via at least one specialized computer network, including networks for tracking serial changes in patients with at least one condition selected from congestive heart failure, coronary artery or ischemic heart disease, cardiac arrhythmias, hypertension, syncope, asthma, diabetes, and other illnesses.

37. A system as set forth in claim 25 in which said higher resolution analysis of health data is integrated into an artificial intelligence system, which includes at least one method selected from an expert system, a neural network and a combination of the methods (a hybrid system).

38. A system as set forth in claim 32 in which said computer network includes at least one of a fuzzy-logic classifier and a dynamic neural network with at least one neuron (unit) for analyzing changes in at least one state of activity of at least one physiological, biological, biophysical, mechanical and genetic system relative to at least one reference value.

39. A system as set forth in claim 25 in which said at least one reference value is represented by a relation (function, distribution) between said reference values and at least one state of at least one physiological, biochemical, biophysical, mechanical, and genetic system.

40. A system as set forth in claim 25 in which said second analysis and processing unit is adapted to track dynamically at least one of information completeness, disease state transition probability matrix, observation (emission) probability matrix, Bayesian probability, Bayesian network, Markov model, hidden Markov model, and probability of a certain disease in all distributed databases in at least one level of detail.

41. A system as set forth in claim 26 in which said communications unit is adapted to continuously send at least one of information, raw data, and derived parameters to said at least one of said acquisition unit and said first and second analysis and processing units.

42. A system as set forth in claim 25 in which said first analysis and processing unit is portable.

43. A system as set forth in claim 26 in which said at least one acquisition unit is implantable.

44. A system as set forth in claim 43 in which said implantable acquisition unit includes processing capability.

45. A system as set forth in claim 25 in which at least one of said first analysis and processing unit and said second analysis and processing unit is a wireless communication device selected from at least of one of a cell phone, smart phone, PDA, Wi-Fi, and other types of radio-transmitters and communication devices.

46. A system useful in healthcare information management comprising a dynamic serial analysis and processing unit for processing health data collected over time using at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Markov model, hidden Markov model, and Mahalanobis distance, pattern recognition, fuzzy logic, neural networks, expert systems, and hybrid artificial intelligence systems to detect serial changes in said at least one primary element (serial analysis) to provide detailed characterization of any abnormal or unstable primary elements.

47. A system as set forth in claim 46 which includes a low resolution analysis and processing unit for analyzing a snapshot of said at least one primary element in low resolution and a communications unit for distributing data respecting said primary elements to at least one computing device for exchanging information between said low resolution analysis unit and said dynamic analysis unit.

48. A system as set forth in claim 46 which includes at least one acquisition unit for collecting health data.

49. A method useful in healthcare information management comprising:
   collecting at least one primary element over a period of time; and
   analyzing serial changes in said at least one primary element of health data using a dynamic serial analysis and processing unit employing at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Markov model, hidden Markov model, and Mahalanobis distance, pattern recognition, fuzzy logic, neural networks, expert systems, and hybrid artificial intelligence systems to provide detailed characterization of serial changes in any abnormal or unstable primary element.

50. A method as set forth in claim 49 in which analyzing said serial changes is performed using a wireless communication device.

* * * * *